(12) United States Patent
Santra

(10) Patent No.: US 12,152,105 B2
(45) Date of Patent: Nov. 26, 2024

(54) POLYETHYLENE GLYCOL-FUNCTIONALIZED TRIGLYCERIDE POLYOL POLYMERS

(71) Applicant: Kansas Soybean Commission, Topeka, KS (US)

(72) Inventor: Santimukul Santra, Pittsburg, KS (US)

(73) Assignee: Kansas Soybean Commission, Topeka, KS (US)

(*) Notice: Subject to any disclaimer, the term of this patent is extended or adjusted under 35 U.S.C. 154(b) by 440 days.

(21) Appl. No.: 17/239,044

(22) Filed: Apr. 23, 2021

(65) Prior Publication Data

US 2021/0388160 A1 Dec. 16, 2021

Related U.S. Application Data

(60) Provisional application No. 63/017,873, filed on Apr. 30, 2020.

(51) Int. Cl.
*C08G 65/331* (2006.01)
*A61K 8/86* (2006.01)
*A61Q 17/04* (2006.01)

(52) U.S. Cl.
CPC ............ *C08G 65/3312* (2013.01); *A61K 8/86* (2013.01); *A61Q 17/04* (2013.01); *A61K 2800/522* (2013.01); *A61K 2800/54* (2013.01)

(58) Field of Classification Search
None
See application file for complete search history.

(56) References Cited

U.S. PATENT DOCUMENTS

| | | |
|---|---|---|
| 2005/0197505 A1 | 9/2005 | Molock et al. |
| 2007/0166270 A1 | 7/2007 | Neuss et al. |
| 2013/0289284 A1 | 10/2013 | Musa et al. |
| 2016/0067296 A1 | 3/2016 | Brownell et al. |

OTHER PUBLICATIONS

Braca et al., "Antioxidant Principles from Bauhinia Tarapotensis", Journal of Natural Products, 2001, pp. 892-895, vol. 64, No. 7.
Ebrahimzadeh et al., "Antioxidant Activity of the Bulb and Aerial Parts of *Ornithogalum sintenisii* L (Liliaceae) at Flowering Stage", Tropical Journal of Pharmaceutical Research, Apr. 2010, pp. 141-148, vol. 9, No. 2.
Kaur et al., "In Vitro Sun Protection Factor Determination of Herbal Oils Used in Cosmetics", Pharmacognosy Research, Jan. 2010, pp. 22-25, vol. 2, No. 1.
Sahasrabudhe et al., "Anti-Hyaluronidase, Anti-Elastase Activity of Garcinia Indica", International Journal of Botany, 2010, pp. 299-303, vol. 6, No. 3.
Thring et al., "Anti-Collagenase, Anti-Elastase and Anti-Oxidant Activities of Extracts from 21 Plants", BMC Complementary and Alternative Medicine, 2009, pp. 1-11, vol. 9, No. 27.

*Primary Examiner* — Nannette Holloman
(74) *Attorney, Agent, or Firm* — Thompson Coburn LLP; Steven M. Ritchey

(57) ABSTRACT

A polyethylene glycol-functionalized triglyceride polyol polymer comprising a glycerol component and three fatty acid components bonded to the glycerol component, wherein at least one of the fatty acid components comprises: a fatty acid chain; a hydroxyl functional group bound to a carbon atom of the fatty acid chain; and a polyethylene glycol-based functional group bound to an adjacent carbon atom of the fatty acid chain; according to Structure I

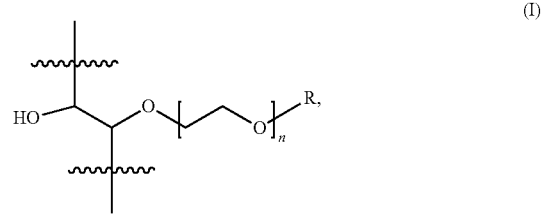

(I)

wherein:
n is from 10 to 40; and
R is selected from the group consisting of H, alkyl, and silyl.

20 Claims, 30 Drawing Sheets

PEG 1K-SBO 3h

Synthesis of Epoxidized Soybean oil (ESBO):

POLYETHYLENE GLYCOL-FUNCTIONALIZED TRIGLYCERIDE POLYOL POLYMERS

CROSS-REFERENCE TO RELATED APPLICATIONS

This application claims the benefit of U.S. Provisional Application Ser. No. 63/017,873 filed on Apr. 30, 2020, which is incorporated herein by reference in its entirety.

FIELD OF THE INVENTION

The present invention is directed to production of polyethylene glycol-functionalized triglyceride polyol polymers and the use thereof (e.g., as a UV absorbing base compound in topical sunscreens compositions).

SUMMARY OF INVENTION

In one embodiment, the present invention is directed to a polyethylene glycol-functionalized triglyceride polyol polymer comprising a glycerol component and three fatty acid components bonded to the glycerol component, wherein at least one of the fatty acid components comprises:
  a fatty acid chain;
  a hydroxyl functional group bound to a carbon atom of the fatty acid chain; and
  a polyethylene glycol-based functional group bound to an adjacent carbon atom of the fatty acid chain;
according to Structure I

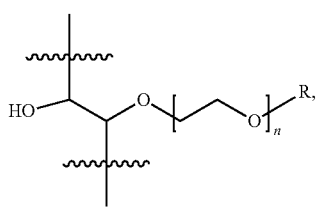

(I)

wherein:
  n is from 10 to 40; and
  R is selected from the group consisting of H, alkyl, and silyl.

In a further embodiment of the foregoing polymer, three of the fatty acid components comprise Structure I.

In a further embodiment of the foregoing polymers, at least one of the fatty acid components comprises more than one Structure I.

In a further embodiment of the foregoing polymers, R is CH$_3$.

In a further embodiment of the foregoing polymers, the fatty acid chain(s) independently comprises between 12 and about 20 carbon atoms.

In a further embodiment of the foregoing polymers, the triglyceride of the polyethylene glycol-functionalized triglyceride polyol polymer is a vegetable oil constituent.

In a further embodiment of the foregoing polymers, the vegetable oil is selected from the group consisting of soybean oil, corn oil, palm oil, sunflower oil, canola oil, sesame oil, peanut oil, olive oil, cottonseed oil, avocado oil, almond oil, walnut oil, flaxseed oil, and combinations thereof.

In a further embodiment of the foregoing polymers, the vegetable oil is soybean oil.

In a further embodiment of the foregoing polymers, which is free of polyethylene glycol groups between the glycerol component and the fatty acid components of the triglyceride.

Another embodiment of the present invention is directed to a topical lotion comprising a base component, wherein the base component comprises any one of the foregoing the polyethylene glycol-functionalized triglyceride polyol polymers.

In a further embodiment of the foregoing lotion, the polyethylene glycol-functionalized triglyceride polyol polymer is at an amount in a range of about 40% to about 80% by weight of the topical lotion.

In a further embodiment of the foregoing lotions, the lotions further comprise an antioxidant isoflavone component.

In a further embodiment of the foregoing lotions, the antioxidant isoflavone component is selected from the group consisting of daidzein, genistein, and combinations thereof.

In a further embodiment of the foregoing lotions, the antioxidant isoflavone component is at an amount in a range of about 2% to about 6% by weight of the topical lotion.

In a further embodiment of the foregoing lotions, the lotions further comprise an antioxidant nanoparticle component.

In a further embodiment of the foregoing lotions, the antioxidant nanoparticle component comprises a metal oxide that is selected from the group consisting of cerium oxide, manganese oxide, iron oxide, and combinations thereof.

In a further embodiment of the foregoing lotions, the antioxidant nanoparticle component is at an amount in a range of about 2% to about 6% by weight of the topical lotion.

In a further embodiment of the foregoing lotions, the lotions further comprise a DNA repair enzyme component.

In a further embodiment of the foregoing lotions, the DNA repair enzyme component is a nucleic acid.

In a further embodiment of the foregoing lotions, the DNA repair enzyme component is at an amount in a range of about 1% to about 4% by weight of the topical lotion.

In a further embodiment of the foregoing lotions, the lotions further comprise an herbal extract component.

In a further embodiment of the foregoing lotions, the herbal extract component is selected from the group consisting of alkaloids, flavonoids, and combinations thereof.

In a further embodiment of the foregoing lotions, the herbal extract component is at an amount in a range of about 1% to about 4% by weight of the topical lotion.

Another embodiment of the present invention is directed to a method of a preparing polyethylene glycol-functionalized triglyceride polyol polymer, the method comprising:
  reacting an expoxidized triglyceride that comprises a glycerol component and three fatty acid components bonded to the glycerol component, wherein at least one of the fatty acid components comprises:
    a fatty acid chain; and
    at least one epoxide functional group bound to two adjacent carbon atoms of the fatty acid chain;
  with a polyethylene glycol-based polymer in the presence of an acidic catalyst to open the epoxide functional group and form:
    a hydroxyl functional group bound to one of said adjacent carbon atoms of the fatty acid chain; and
    a polyethylene glycol-based functional group bound to the other of said adjacent carbon atoms of the fatty acid chain;

according to Scheme I

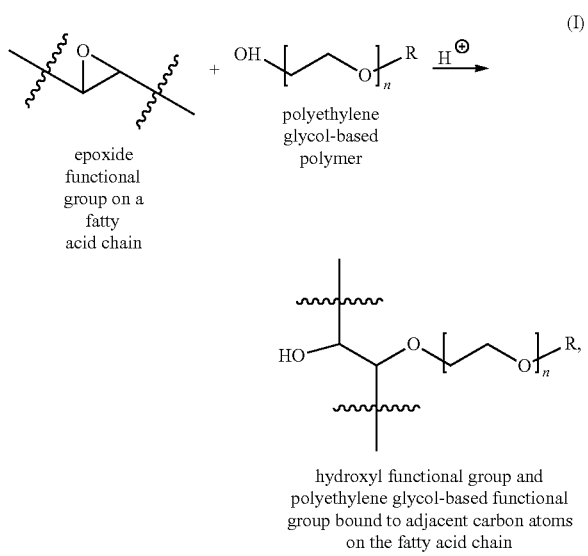

wherein:
n is from 10 to 40 and
R is selected from the group consisting of H, alkyl, and silyl;
thereby producing the polyethylene glycol-functionalized triglyceride polyol polymer.

In a further embodiment of the foregoing method, the three of the fatty acid components comprise the hydroxyl functional group bound to one of said adjacent carbon atoms of the fatty acid chain and the polyethylene glycol-based functional group bound to the other of said adjacent carbon atoms of the fatty acid chain.

In a further embodiment of the foregoing methods, at least one of the fatty acid components comprises more than one of the hydroxyl functional groups and more than one of the polyethylene glycol-based functional groups.

In a further embodiment of the foregoing methods, R is $CH_3$.

In a further embodiment of the foregoing methods, the fatty acid chain(s) independently comprises between 10 and about 20 carbon atoms.

In a further embodiment of the foregoing methods, the triglyceride of the epoxidized triglyceride is a vegetable oil constituent.

In a further embodiment of the foregoing methods, the vegetable oil is selected from the group consisting of soybean oil, corn oil, palm oil, sunflower oil, canola oil, sesame oil, peanut oil, olive oil, cottonseed oil, avocado oil, almond oil, walnut oil, flaxseed oil, and combinations thereof.

In a further embodiment of the foregoing methods, the vegetable oil is soybean oil.

In a further embodiment of the foregoing methods, which is free of polyethylene glycol groups between the glycerol component and the fatty acid components of the triglyceride.

In a further embodiment of the foregoing methods, the acidic catalyst is selected from the group consisting of tetrafluoroboric acid, tetrafluoroboric acid ether complex, and combinations thereof.

In a further embodiment of the foregoing methods, the reaction is conducted in the absence of a solvent.

In a further embodiment of the foregoing methods, the reaction is conducted in the presence of a solvent.

In a further embodiment of the foregoing methods, the reaction is conducted at a temperature in a range about 50° C. and about 60° C.

DETAILED DESCRIPTION OF INVENTION

Figure 1:
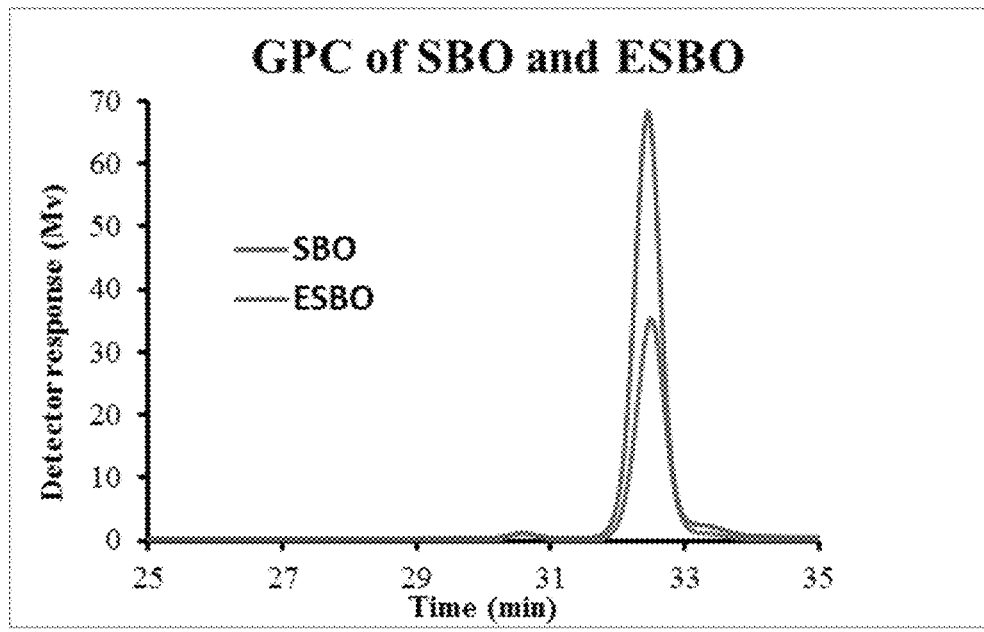
FIG. 1 is a graph of the weight average molecular weight (Mw) of an expoxidized soybean oil (ESBO) synthesized in accordance with the claimed invention compared to that of a commercially available soybean oil (SBO).

In one embodiment, the present invention is directed to a soybean-based biocompatible topical lotion, which is amphiphilic in nature. In particular, a soybean oil-based amphiphilic polymer (i.e., polyethylene glycol (PEG) functionalized soybean polyol polymer) and that is used in a base cream for the formulation of a topical lotion. In one embodiment, the lotion is a multifunctional anti-oxidant topical lotion comprising two soybean derived antioxidant molecules—Daidzein and Genistein, usually known as isoflavones—which scavenge free radicals resulting from exposure to sunlight. In another embodiment, the lotion comprises antioxidant cerium oxide nanoparticles (nanoceria) and an herbal extract, which are believed to enhance the free radical scavenging property of the formulated base cream and to improve the phenolic and flavonoid content of the lotion. Also, the herbal extract is believed to have anti-cancer activity that is believed to protect skin from skin cancer. It is believed that the most commercially desirable applications of such lotions are for sun screen lotions and cosmetics.

The PEGylated SBO polyol polymer is amphiphilic due to the presence of PEG on the surface. The soybean oil (SBO) may be epoxidized using formic acid and hydrogen peroxide. The resulting epoxidized soybean oil (ESBO) may be purified before synthesizing PEGylated polyol polymer. Experimental results to date suggest that by changing the molecular weight of the monomethyl PEG polymer (MeO-PEG-OH), the resulting SBO-PEG polymer receives different degrees of water solubility and dispersity.

Polyethylene Glycol-Functionalized Triglyceride Polyol Polymer

More particularly, in one embodiment, the present invention is directed to a polyethylene glycol-functionalized triglyceride polyol polymer comprising a glycerol component and three fatty acid components bonded to the glycerol component, wherein at least one of the fatty acid components comprises:

a fatty acid chain;
a hydroxyl functional group bound to a carbon atom of the fatty acid chain; and
a polyethylene glycol-based functional group bound to an adjacent carbon atom of the fatty acid chain;

according to Structure I

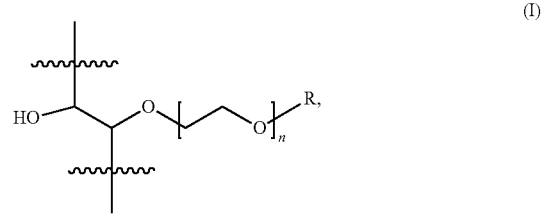

wherein:
n is from 10 to 40; and
R is selected from the group consisting of H, alkyl, and silyl.

Locations of the Polyethylene Glycol Groups

As indicated above, it is desired for a polyethylene glycol-based functional group to be bound to an adjacent carbon atom of the fatty acid chain. That said, in one embodiment, it is desirable for the polymer to be free of polyethylene glycol groups between the glycerol component and the fatty acid components of the triglyceride.

Fatty Acid Components Bonded to the Glycerol Component

In one embodiment, the fatty acid chain(s) independently comprises between 12 and about 20 carbon atoms.

Structure I

In one embodiment, each of the three of the fatty acid components comprise the Structure I. In another embodiment, at least one of the fatty acid components comprises more than one Structure I.

In an embodiment, R is $CH_3$.

Triglyceride

In an embodiment, the triglyceride of the polyethylene glycol-functionalized triglyceride polyol polymer is a vegetable oil constituent. For example, the vegetable oil may be selected from the group consisting of soybean oil, corn oil, palm oil, sunflower oil, canola oil, sesame oil, peanut oil, olive oil, cottonseed oil, avocado oil, almond oil, walnut oil, flaxseed oil, and combinations thereof. In one embodiment, the vegetable oil is soybean oil.

Topical Lotion

Base Component

Another embodiment of the present invention is directed to a topical lotion comprising a base component, wherein the base component comprises any one of the foregoing the polyethylene glycol-functionalized triglyceride polyol polymers. For example, the polyethylene glycol-functionalized triglyceride polyol polymer may be at an amount in a range of about 40% to about 80% by weight of the topical lotion.

Antioxidant Isoflavone Component

In an embodiment, the lotion comprises an antioxidant isoflavone component. For example, the antioxidant isoflavone component may be selected from the group consisting of daidzein, genistein, and combinations thereof. The antioxidant isoflavone component may be at an amount in a range of about 2% to about 6% by weight of the topical lotion.

Antioxidant Nanoparticle Component

In an embodiment, the lotion comprises an antioxidant nanoparticle component. For example, the antioxidant nanoparticle component comprises a metal oxide that is selected from the group consisting of cerium oxide, manganese oxide, iron oxide, and combinations thereof. The antioxidant nanoparticle component may be at an amount in a range of about 2% to about 6% by weight of the topical lotion.

DNA Repair Enzyme Component

In an embodiment, the lotion comprises a DNA repair enzyme component such as a nucleic acid. The DNA repair enzyme component may be at an amount in a range of about 1% to about 4% by weight of the topical lotion.

Herbal Extract Component

In an embodiment, the lotion comprises an herbal extract component. For example, the herbal extract component may be selected from the group consisting of alkaloids, flavonoids, and combinations thereof. The herbal extract component may be at an amount in a range of about 1% to about 4% by weight of the topical lotion.

Preparing a Polyethylene Glycol-Functionalized Triglyceride Polyol Polymer

In one embodiment, the present invention is directed to a method of preparing a polyethylene glycol-functionalized triglyceride polyol polymer, the method comprising:
 reacting an expoxidized triglyceride that comprises a glycerol component and three fatty acid components bonded to the glycerol component, wherein at least one of the fatty acid components comprises:
  a fatty acid chain; and
  at least one epoxide functional group bound to two adjacent carbon atoms of the fatty acid chain;
 with a polyethylene glycol-based polymer in the presence of an acidic catalyst to open the epoxide functional group and form:
  a hydroxyl functional group bound to one of said adjacent carbon atoms of the fatty acid chain; and
  a polyethylene glycol-based functional group bound to the other of said adjacent carbon atoms of the fatty acid chain;
 according to Scheme I

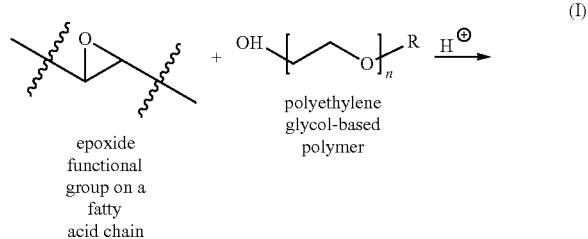

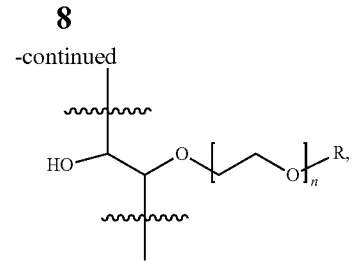

hydroxyl functional group and polyethylene glycol-based functional group bound to adjacent carbon atoms on the fatty acid chain wherein:
 n is from 10 to 40 and
 R is selected from the group consisting of H, alkyl, and silyl;
thereby producing the polyethylene glycol-functionalized triglyceride polyol polymer as described in any of the foregoing embodiments.

In an embodiment, the acidic catalyst is selected from the group consisting of tetrafluoroboric acid, tetrafluoroboric acid ether complex, and combinations thereof.

In an embodiment, the reaction is conducted in the absence of a solvent.

In an embodiment, the reaction is conducted in the presence of a solvent.

In an embodiment, the reaction is conducted at a temperature in a range about 50° C. and about 60° C.

EXAMPLES

Example I—Production and Characterization of Expoxidized Soybean Oil (ESBO)

A. Procedure for Producing ESBO

Figure 19:
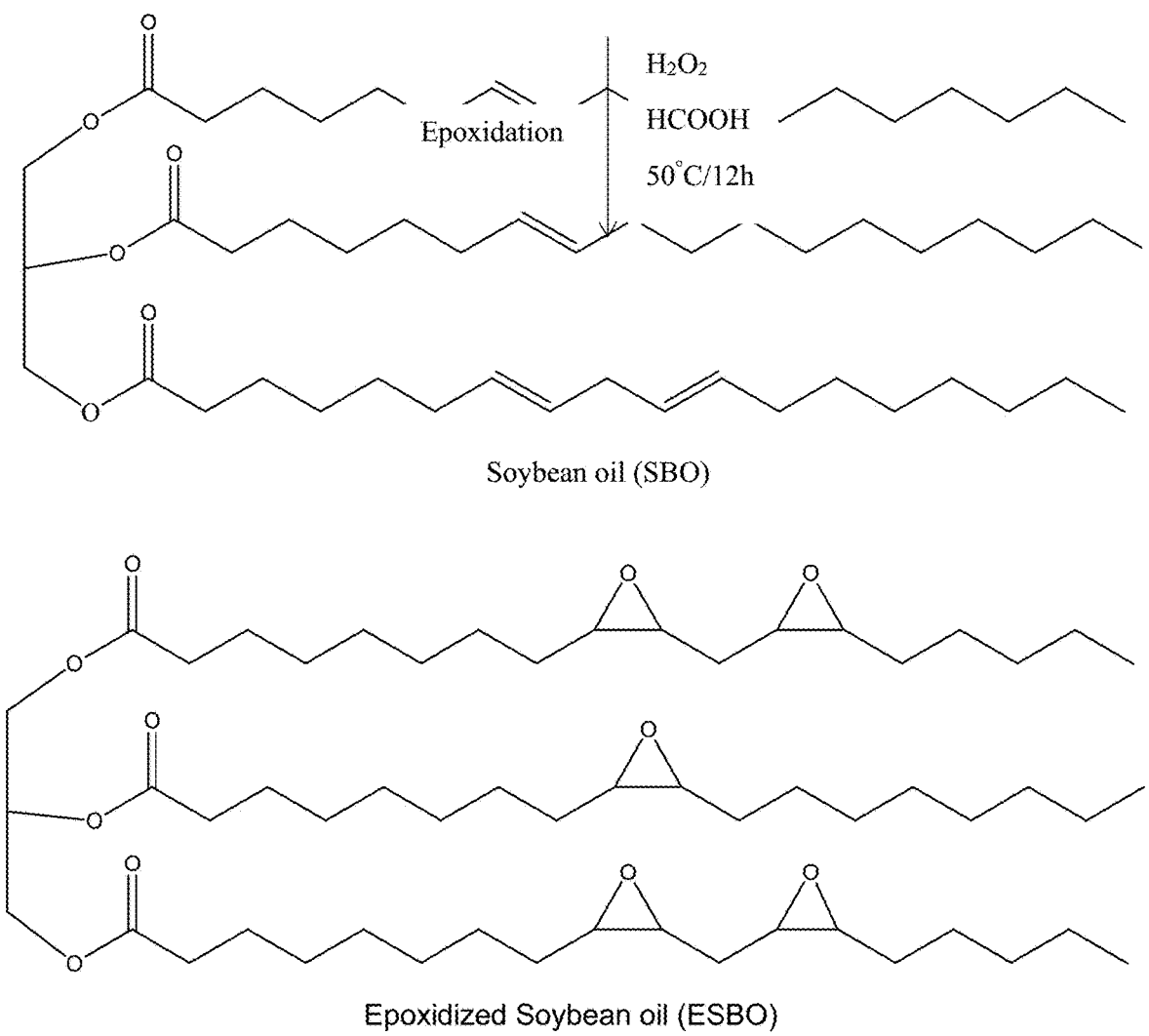
FIG. 19 depicts the synthesis of an expoxidized soybean oil (ESBO) from commercially available soybean oil (SBO).

Soybean oil and a catalytic amount of formic acid (HCOOH) were added to a round bottom flask, heated in a water bath at 50° C., and mechanically stirred at the speed of 550 rpm. To start the epoxidation, hydrogen peroxide ($H_2O_2$, 30%) was gradually added into the mixture. The mole ratios of carbon double bonds to hydrogen peroxide ($C=C:H_2O_2$) was 1:1.7. The reaction was continued for 12 hours and the constant temperature was maintained throughout the reaction. After completion of reaction, the mixture was cooled and neutralized by water. Diethyl ether was used to enhance the separation of the oil phase from aqueous phase. This was repeated thrice and the final product (ESBO) was dried. FIG. 19 illustrates that double bonds on SBO were epoxidized using hydrogen peroxide and formic acid. The synthesis of ESBO was done three times to confirm the repeatability and the resulting ESBO was characterized using the techniques described below.

B. Characterization of Synthesized ESBO

1. Epoxy Oxygen Content (EOC)

The EOC number of the synthesized ESBO was measured by following the standard literature method (Instrument: Metrohm Titrator 719, Method: ACS PER-OXI) and was found to be 7.15 weight %. This value is very close to literature reported value (~7.2 weight %), indicating the successful formation of ESBO.

2. Gel Permeation Chromatography (GPC)

The weight average molecular weight ($M_w$) of the synthesized ESBO was measured using GPC (SIL-20A, Shimadzu Inc.) and compared with that of SBO. The tetrahydrofuran (THF) was used as mobile phase and the data was plotted against polystyrene polymer standard. The results are presented in the FIG. 1. Theoretically, in GPC, the higher molecular weight chemical species comes first due to the lower retention time in the GPC column. The results showed that the formation of higher molecular weight ESBO (calculated molecular weight: 1059 Da) was eluted faster when compared with the starting SBO (calculated molecular weight: 909 Da). The formation of pure single band for ESBO was further confirmed for the 100% conversion of SBO into ESBO.

3. Fourier Transform Infrared (FTIR) Spectroscopy

Figure 2:
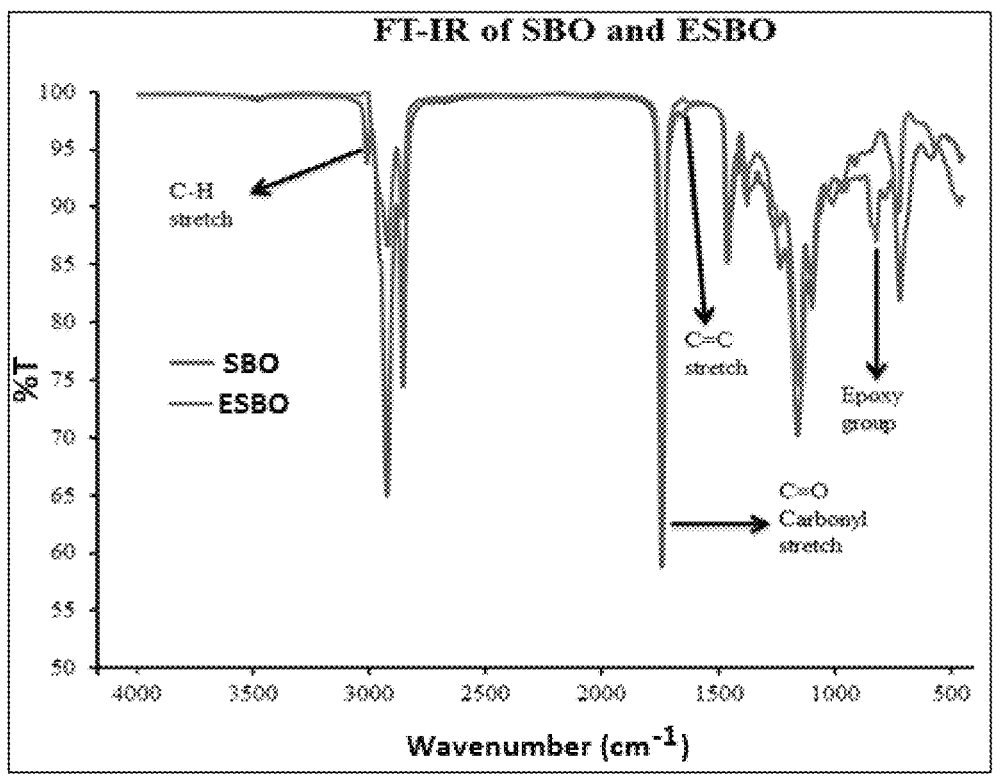
FIG. 2 is comparison of FTIR spectra of the SBO and ESBO.

The Fourier transform infrared (FTIR) spectra of both SBO and ESBO were recorded using PerkinElmer's Spectrum Two spectrometer. The scanning range covered is 4000 to 500 $cm^{-1}$ using neat samples. FTIR spectra of SBO and ESBO are shown in FIG. 2. The characteristic epoxy group peak is observed in ESBO spectrum at 831 $cm^{-1}$. The carbonyl stretch was found at 1746 $cm^{-1}$ in both the cases. The C=C stretch and C=C—H stretch are the characteristic bands for double bond in SBO. Therefore, the formation of epoxy band at 831 $cm^{-1}$ in the ESBO spectrum and disappearance C=C stretching band in the SBO spectrum further confirms for the formation of epoxidized SBO.

Figure 3:
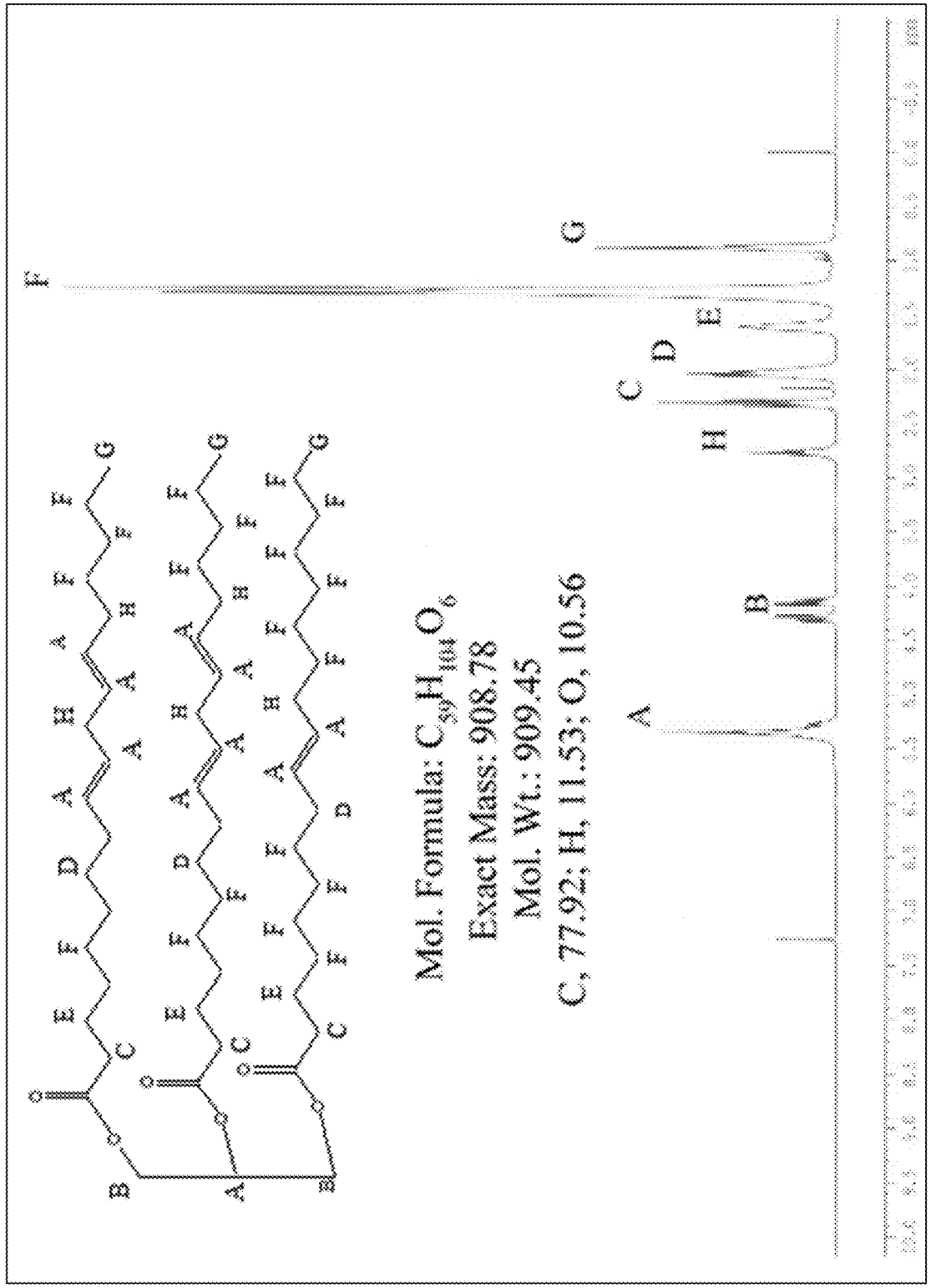
FIG. 3 is a $^1H$ NMR spectrum of the SBO.
Figure 4:
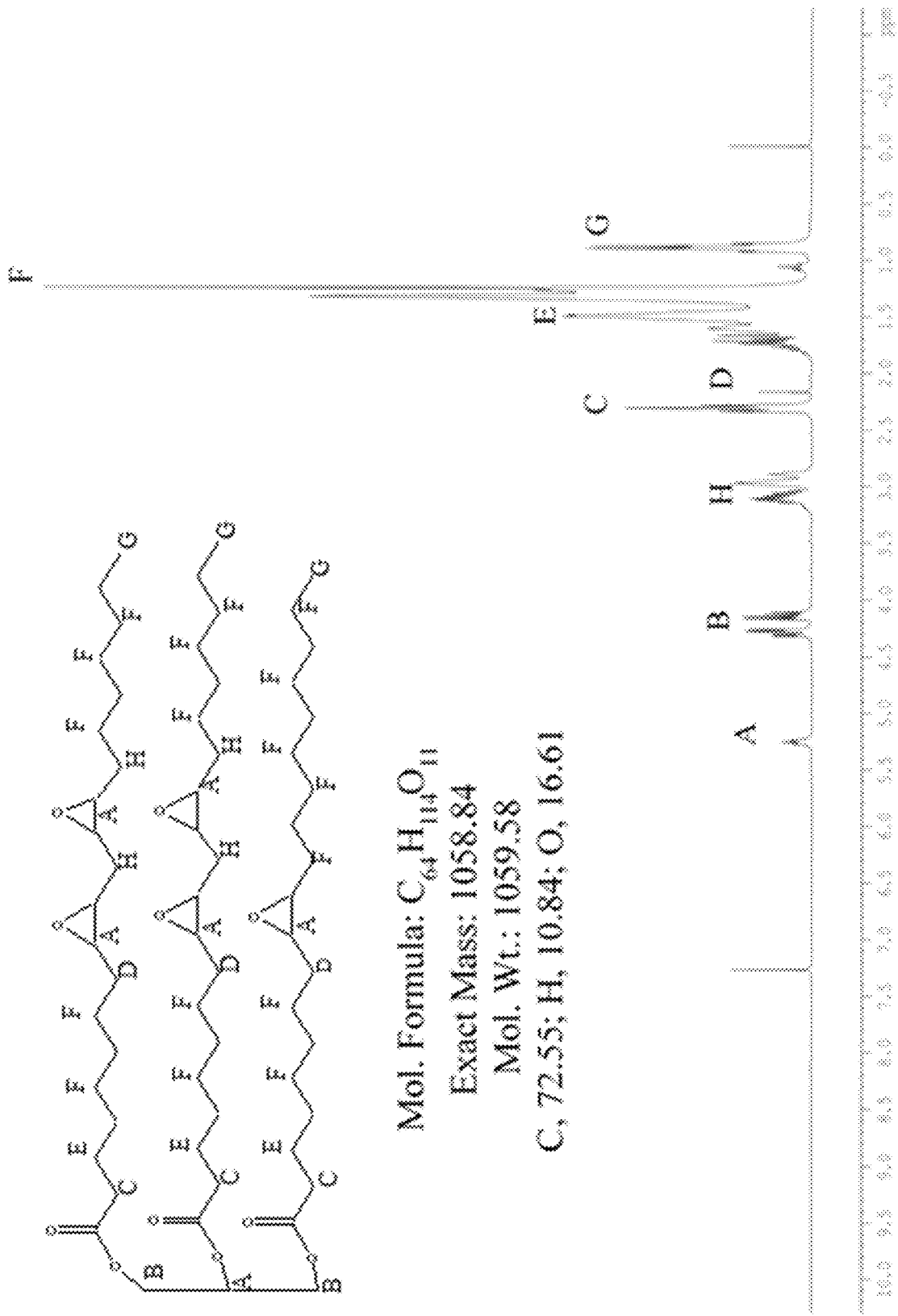
FIG. 4 is a $^1H$ NMR spectrum of the ESBO.

4. $^1$H Nuclear Magnetic Resonance (NMR) Spectroscopy $^1$H NMR spectra of the synthesized ESBO and SBO were recorded using Bruker 300 MHz proton NMR with chloroform-d as solvent. The NMR spectrum provides quantitative structural information of the compound under experiments. $^1$H NMR spectra of SBO and ESBO are presented in FIG. 3 and FIG. 4. A representative structure of the SBO and ESBO are included in the figures to illustrate the assignment of peaks. The appearance of Peak A, corresponding to C=C in SBO and the reduction of same peak in ESBO confirmed that the double bond reacted to form an epoxy group in ESBO. Similarly, Peak H corresponds to the =CH—$CH_2$—CH=group in SBO, whereas for ESBO the double bond had reacted to form an orixane ring, which results in multiple peaks for the latter. The peaks assigned to the adjacent groups associated with double bonds showed the significant change in the spectra.

Example II—Production and Characterization of Amphiphilic Soybean Polymer

A. Design, Synthesis and Characterization of Amphiphilic Soybean Polymer

Figure 20:
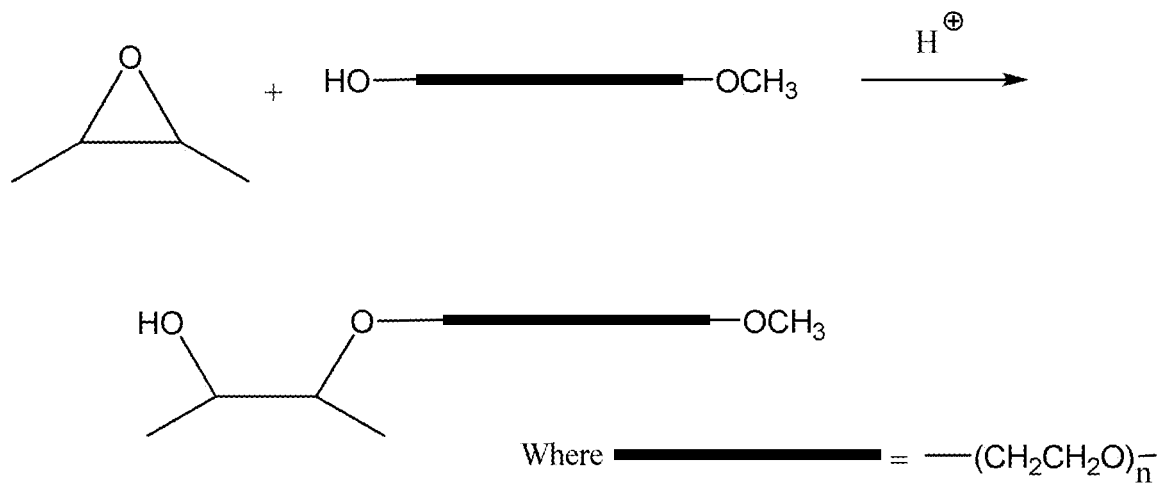
FIG. 20 depicts the general reaction of the ring opening addition of PEG-MME to the epoxy groups of ESBO.

The monomethyl ethers of PEG (PEG-MME, Mw=1K and 4K)) polymer will be used to conjugate with epoxidized soybean oil in order to prepare biocompatible base support (PEGylated soybean polymer, PSP) for the synthesis of antioxidant topical lotion for skin care, especially as a sunscreen lotion. This adduct PSP will represent around 90% of the topical lotion composition. In principle, the addition of PEG-MME to epoxidized soybean oil (ESBO) is based on the fundamental reaction of ring opening of epoxy groups by hydroxyl groups in acidic catalysis (FIG. 20).

Figure 21:
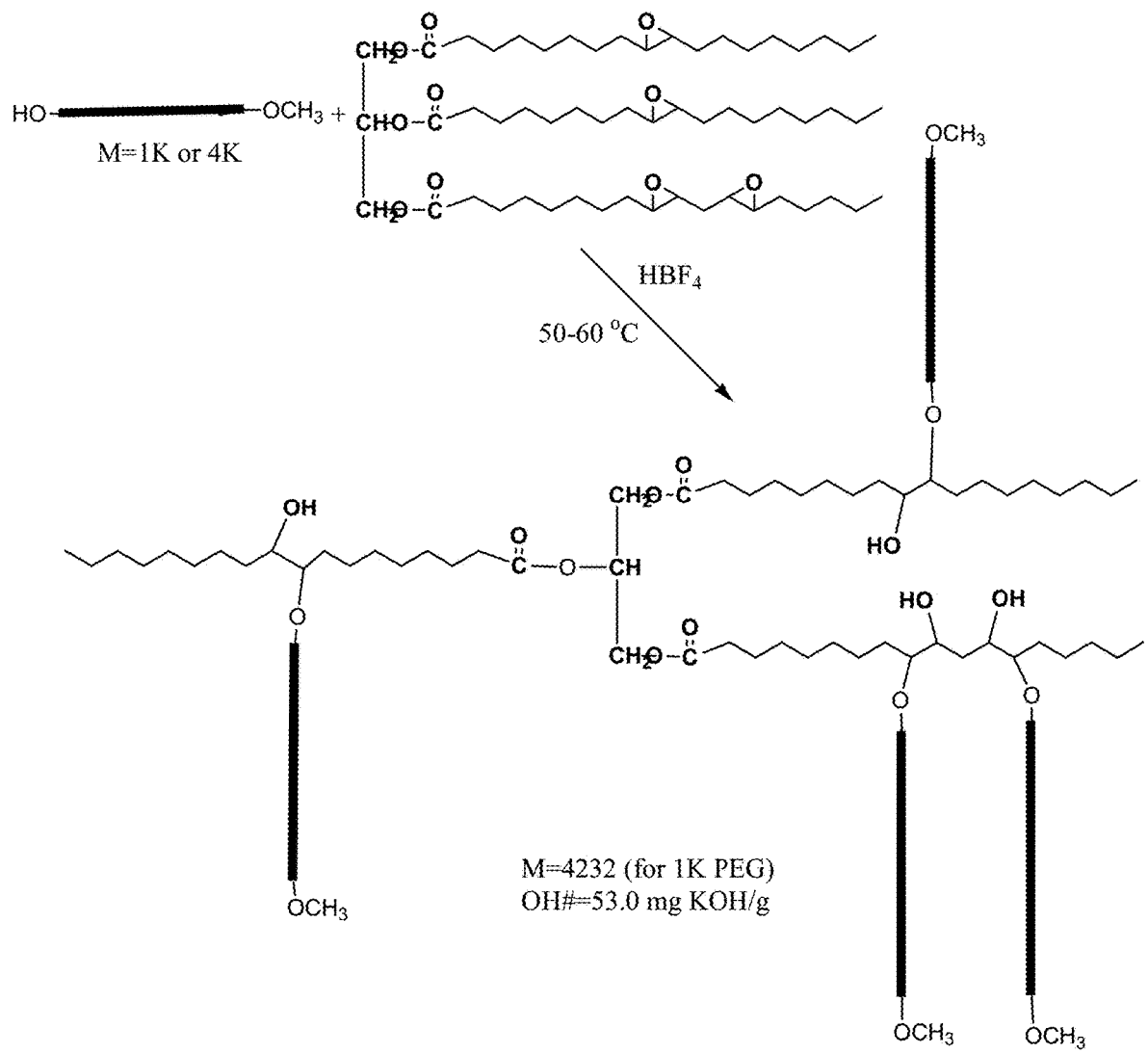
FIG. 21 depicts the general reaction of the addition of the PEG-MME to ESBO.

One of the best catalysts of this reaction is tetrafluoroboric acid ($HBF_4$), a well-known superacid and commercially available as aqueous solution or as complex with diethyl ether. To avoid the ring opening of epoxidic groups with water, the complex of $HBF_4$ with diethyl ether ($HBF_4*Et_2O$) is believed to be preferred. The general reaction of PEG-MME with ESBO is presented in FIG. 21.

1. General Synthesis Procedure

Figure 5:
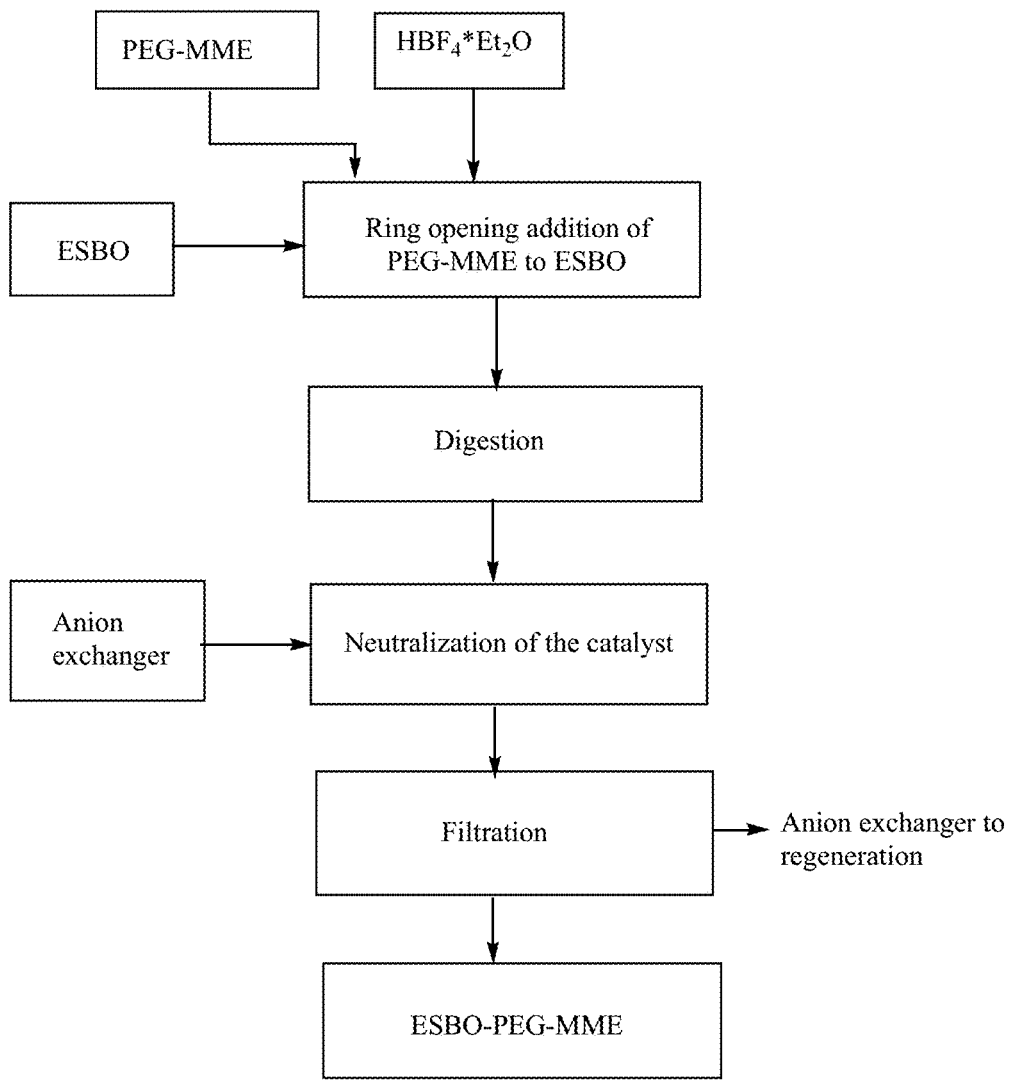
FIG. 5 is a flow chart of the reaction of PEG-MME with ESBO in the absence of a solvent.

To the molten PEG-MME or to a solution of PEG-MME in a solvent, at 50-60° C., in the presence of 0.5% $HBF_4*Et_2O$ as a catalyst, under efficient stirring, liquid ESBO was added stepwise over the period of one hour. The reaction is exothermal and needs periodically cooling. After the addition of ESBO, the reaction mass was maintained at 50-60° C. for at least 2-3 hours to ensure the digestion of the reaction mass (in this period of time, the last unreacted epoxy groups react), and then was continued for 12 hours. The acid catalyst was removed by neutralization with a weak basic anion exchanger, followed by filtration in the absence of solvent (at 50-60° C.) or in the presence of a solvent (at room temperature). After separation of the anion exchanger, the solvent (if it was present) and some trace of water were removed by vacuum distillation. The flow charts for addition of PEG-MME to ESBO in the absence and in the presence of solvents set forth in FIGS. 5 and 6, respectively. During the synthesis, a molar ratio [epoxy]/[hydroxyl] of 1/1 was used, and the yield of adduct was a relatively high 70-90%. It was interesting that the yield of adduct formation was higher in solvents than in the absence of solvents at [epoxy]/[hydroxyl]=1/1.

Figure 6:
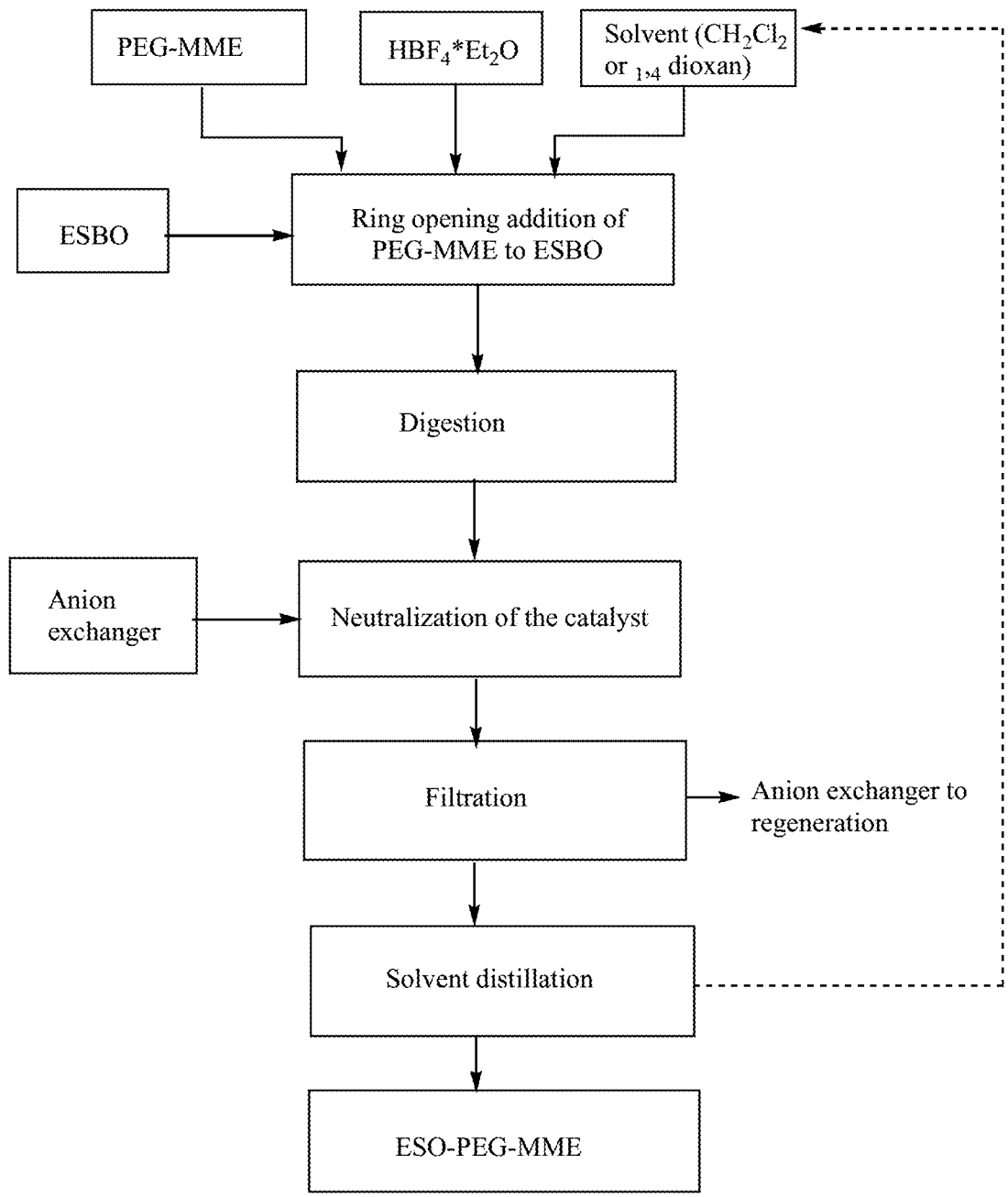
FIG. 6 is a flow chart of the reaction of PEG-MME with ESBO in the presence of solvents.

Because, the filtration step in the absence of solvent was difficult and needed a long filtration time, we tested a variation of the synthesis in the presence of solvents (methylene chloride and 1,4-dioxan) as shown in FIG. 6. The mentioned solvents are good for cationic processes. This synthesis involved some additional steps due to solvent distillation and recycling but the filtration step was very rapid. Although effective, the recycling of solvent tends to increase the production cost.

Another variation is to use water as a solvent for filtration. Unfortunately, the filtration was rapid only at a concentration of adduct in water of 30% or less. At higher concentrations, the filtration was slow. The advantage of using water is that recycling is unnecessary; only a simple distillation after filtration is required. The product can be filtered efficiently, in short time, by using a filter under pressure, at around 50-60° C.

2. Synthesis of PEG-SBO-Polyester Polyols (Alternate Method)

Amphiphilic SBO polymer was synthesized, which is surprisingly water dispersible. Specifically, polyethylene glycol (MME-PEG, 1,000 and 4000 Da)-conjugated SBO was synthesized directly from ESBO using the above-mentioned protocol.

In a typical organic synthesis process, 0.5 g of ESBO and 2.19 g MME-PEG (1:4.8 equivalent ratio) were mixed along with catalytic amount of $HBF_4$ catalyst. The reaction mixture was conducted at 75-80° C. At different times, samples were collected for standardization of this polymerization reaction with the help of GPC, FT-IR, NMR and others. Epoxy oxygen content (EOC) and hydroxyl number calculation experiments confirmed that the reaction was more than 90% completed within 5 h of reaction.

B. Characterizations of Synthesized Amphiphilic Soybean Polymer

1. Epoxy Oxygen Content (EOC)

EOC number of the synthesized ESBO was found to be 7.15 weight %. EOC number of the PEG 1K-SBO was found to be 0.1 weight % indicating that ring-opening of epoxy group had occurred.

2. Hydroxyl Number (#OH)

Hydroxyl number denotes the number of hydroxyl groups present in the sample.

The hydroxyl number of the synthesized PEG 1K-SBO was found to be 184.06 mg KOH/g, indicated the successful synthesis of SBO-PEG polyester polyols.

3. Gel Permeation Chromatography

Figure 7:
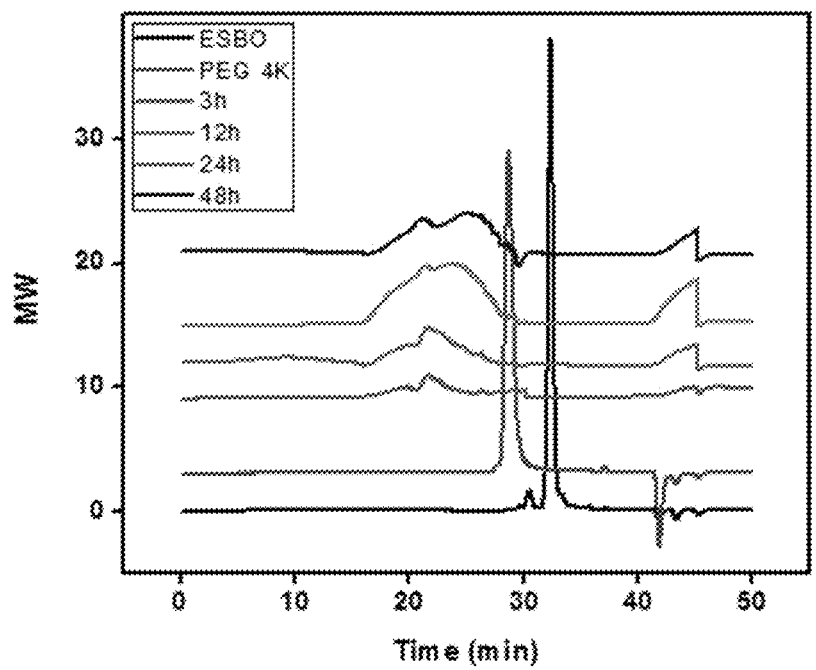
FIG. 7 shows the gel permeation chromatography (GPC) results of the PEG-SBO-Polyester polyols.

The weight average molecular weight ($M_w$) of the synthesized PEG-SBO-polyester was measured using GPC (SIL-20A, Shimadzu Inc.). The tetrahydrofuran (THF) was used as mobile phase and the data was plotted against polystyrene polymer standard. The results are presented in the FIG. 7. Time dependent GPC chromatograms show the successful formation of the polymer within 3 h of reaction.

4. Fourier Transform Infrared (FTIR) Spectroscopy

Figure 8:
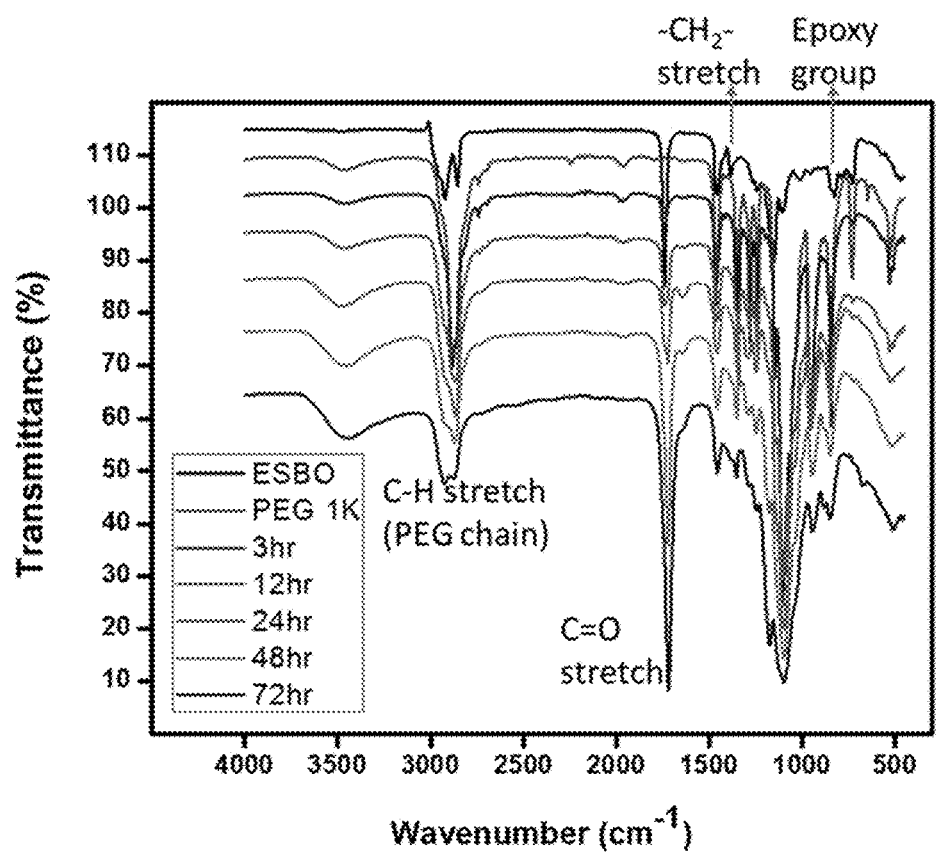
FIG. 8 show the FTIR results of the PEG-SBO-Polyester polyols.

The Fourier transform infrared (FTIR) spectra of the polymers from different time points were recorded and presented in FIG. 8. The results confirmed the formation of polyol polymer with time, as the FT-IR bands at 3320 cm$^{-1}$ for hydroxyl groups formation were become more visible with time.

5. $^1$H Nuclear Magnetic Resonance (NMR) Spectroscopy

Figure 9:
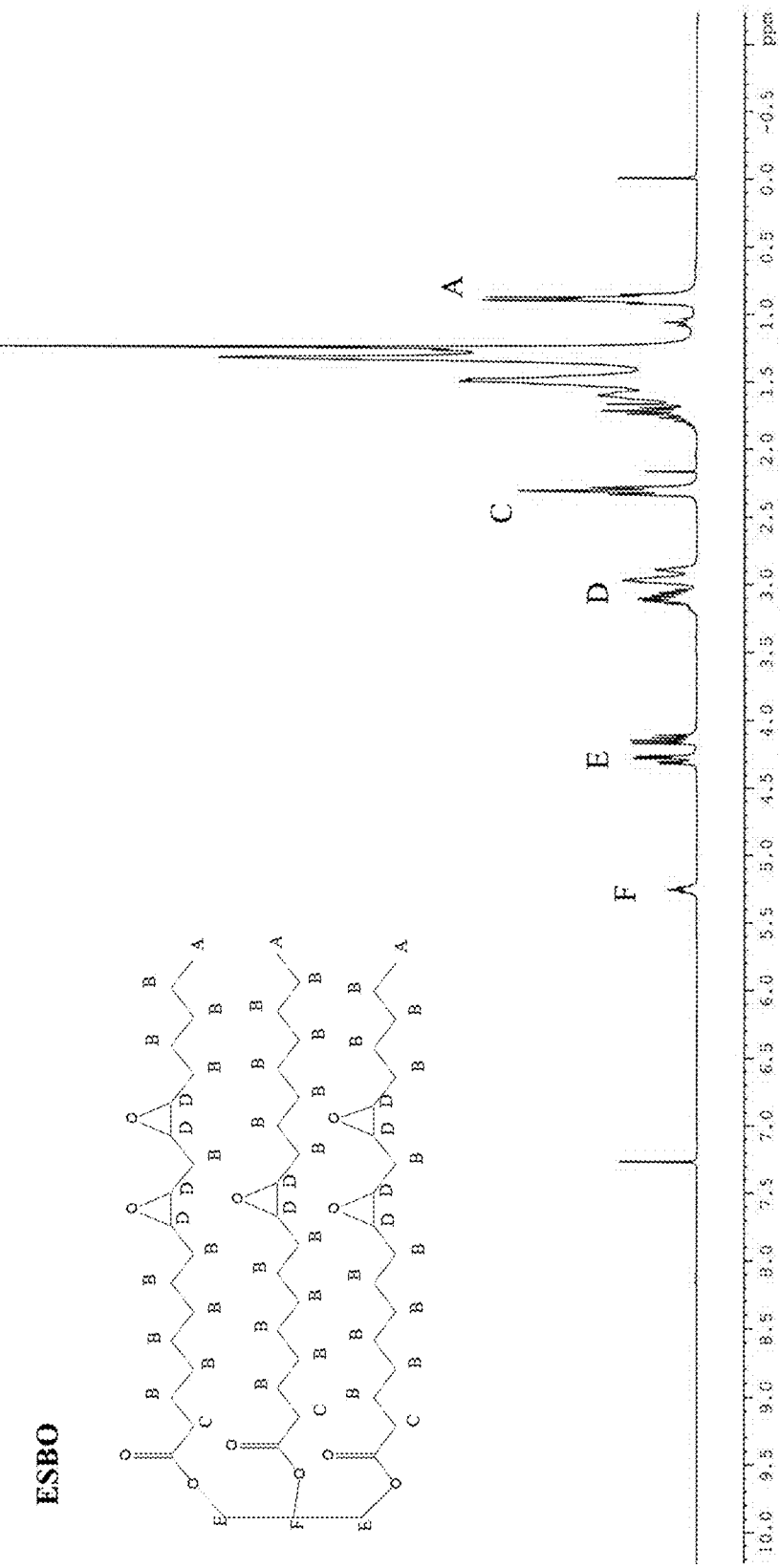
FIG. 9 is a $^1H$ NMR spectrum of the synthesized ESBO showing the formation of the epoxy ring.
Figure 10:
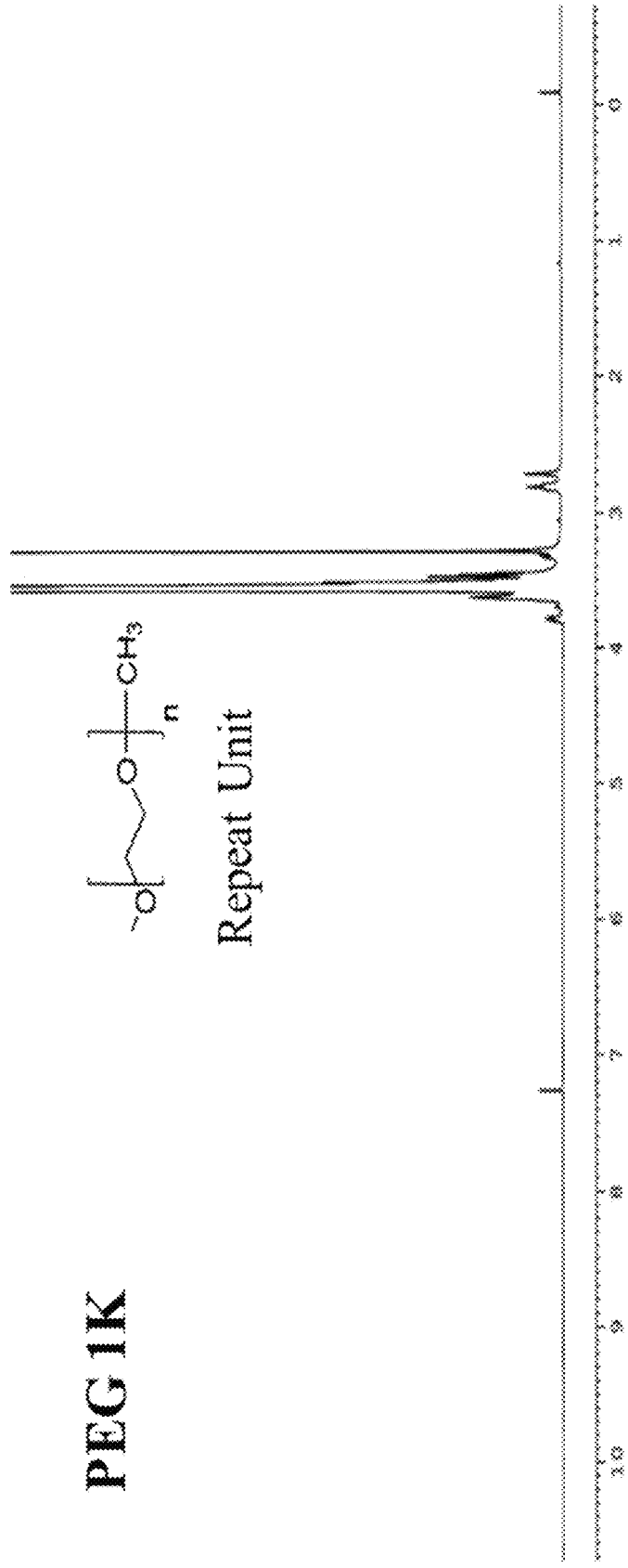
FIG. 10 is a $^1H$ NMR spectrum of the PEG (1K) polymer.
Figure 11:
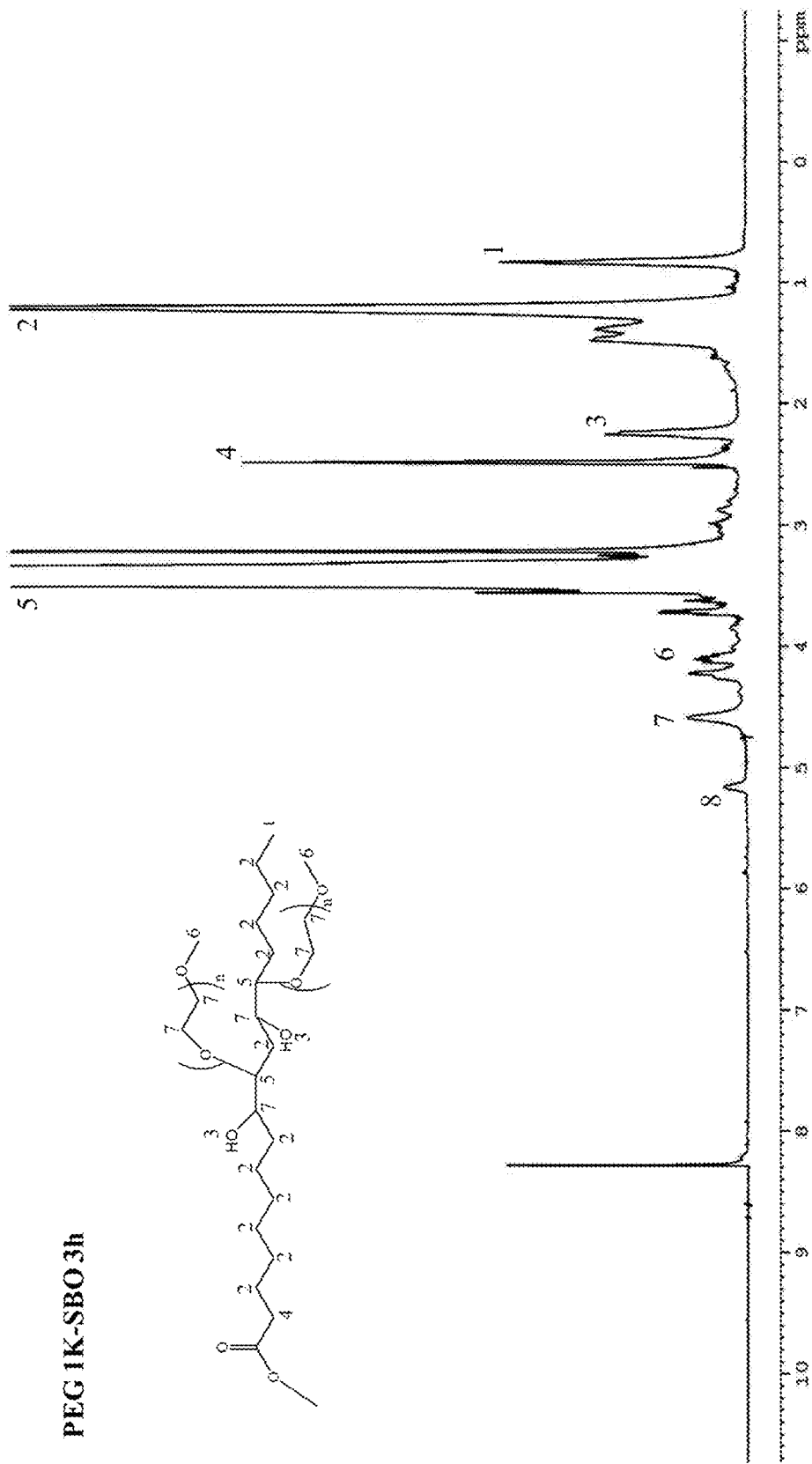
FIG. 11 is a $^1H$ NMR spectrum of the synthesized SBO showing the formation of the hydroxyl groups and reduction of the epoxy ring.

The $^1$H NMR spectra of the synthesized ESBO showing the formation of the epoxy ring is in FIG. 9. The $^1$H NMR spectra of PEG (1K) is in FIG. 10. The $^1$H NMR spectra of the synthesized PEG-SBO Polyester polyols, shows the formation of hydroxyl groups and reduction of epoxy ring in FIG. 11.

6. Thermogravimetric Analysis

Figure 12:
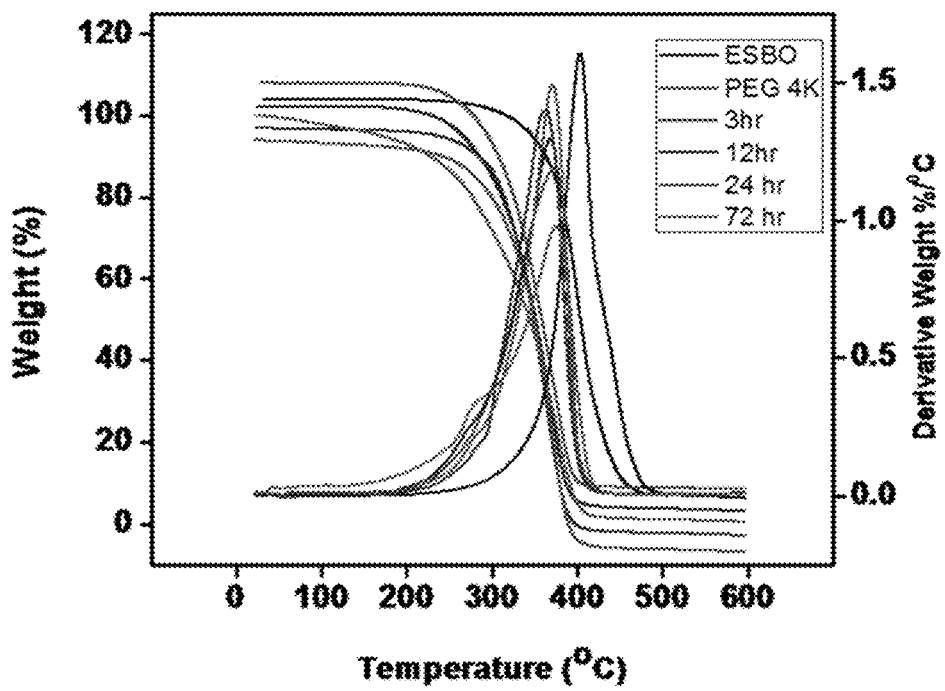
FIG. 12 shows thermogravimetric analysis (TGA) of the synthesized SBO polymers.

Thermogravimetric analysis indicates the degradation temperature of the polymer and the percentage weight loss of the sample. Moderate thermal stability of the synthesized SBO polymer was observed in TGA analysis of FIG. 12.

7. Differential Scanning Calorimetry (DSC)

Figure 13:
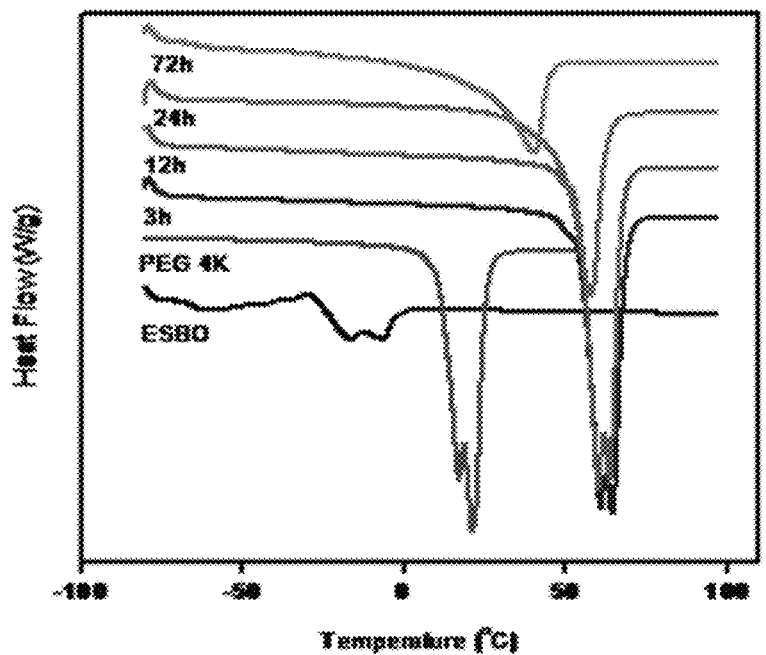
FIG. 13 shows the differential scanning calorimetry (DSC) chromatograms of synthesized SBO polymers.

SBO, ESBO and PEG-SBO polymer (soybean polyol) are characterized by DSC to know the crystalline behavior and melting point of the samples to understand their physiochemical and mechanical properties. As shown in FIG. 13, the polymer sample has similar properties as that of PEG.

Example III—UV Light Protection Study of PEG-SBO Polymers

A. Stability of PEG-SBO Polymer (Base) in the Presence of UV-Light

Figure 14:
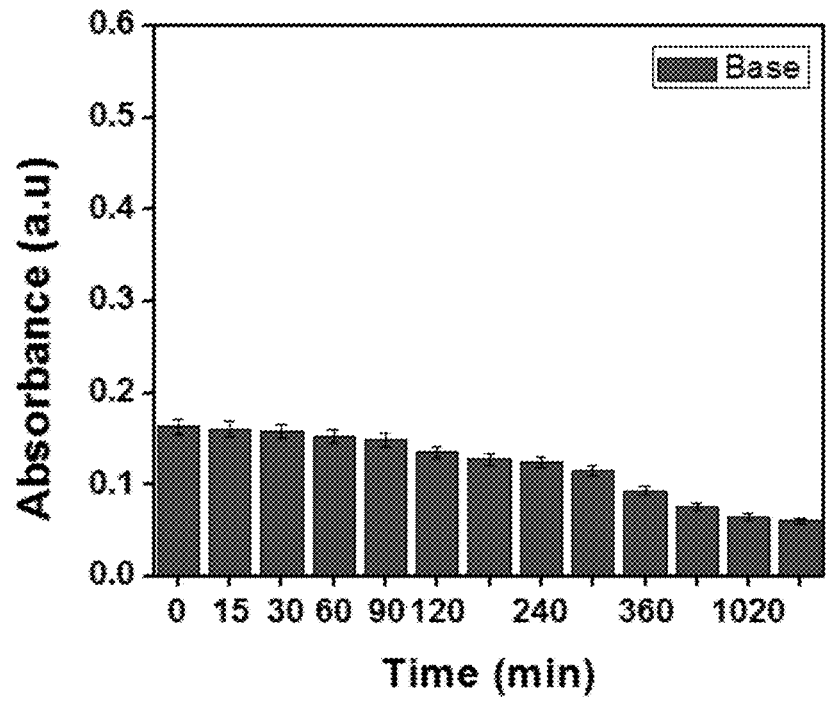
FIG. 14 shows the UV absorbance pattern of PEG-SBO polymer (1K Da) in a base cream in the presence of UV light over time, which shows there is little change in the absorbance over time that indicates stability of the polymer in the presence of UV light.

After synthesis of PEG-SBO polymer, the stability of the PEG-SBO polymer in the presence of UV light (UVA: 315-400 nm and UVB: 280-315 nm) was evaluated. In this case, the PEG-SBO polymer (PEG 1K) to the UV source for 24 h and data were collected in a timely pattern. Results indicated that there is no to little change in the polymers own absorbance, even in the presence of prolonged UV light. This indicated the UV-resistant and higher stability of the PEG-SBO polymer in the presence UV light, as shown in FIG. 14.

B. Stability of DiI Dye in the Presence of UV-Light

Figure 15:
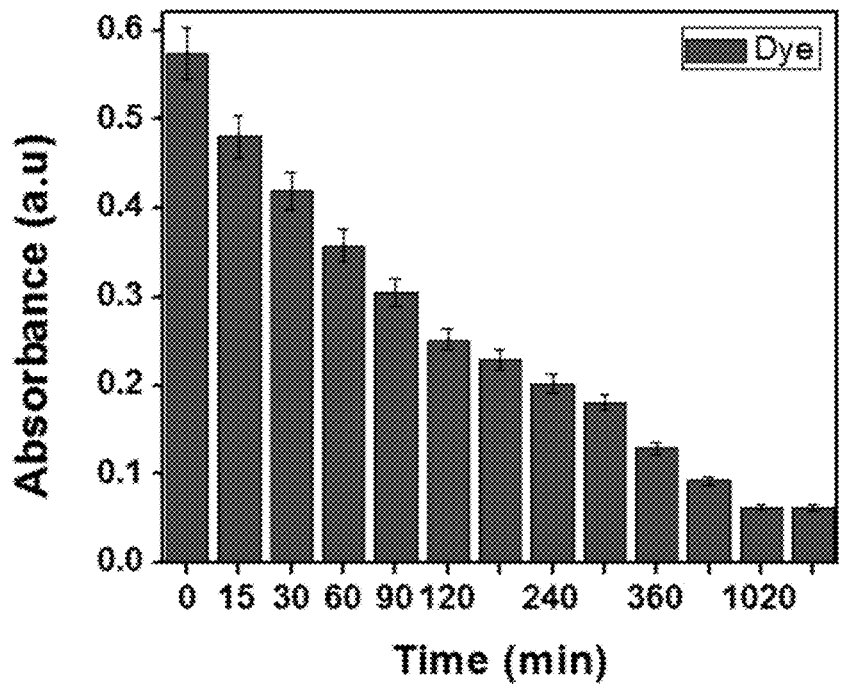
FIG. 15 shows the absorbance pattern of DiI dye in the presence of UV light, which shows there is much change in the absorbance of the DiI dye over time that indicates the sensitivity of the dye in the presence of UV light.

The stability of DiI dye in the presence of UV light (UVA: 315-400 nm and UVB: 280-315 nm), which represents human skin because it is very sensitive to UV rays was evaluated. The DiI dye to the UV source for 24 h and data was collected in a timely pattern. As shown in FIG. 15, the dye was quenched very rapidly in the presence of UV light. About 80% of dye got quenched within 2 h of time. This indicated that dye is not UV-resistant and is easily affected (quenched) by UV-light, which is representing the sensitivity of human skin to sun rays.

Figure 16:
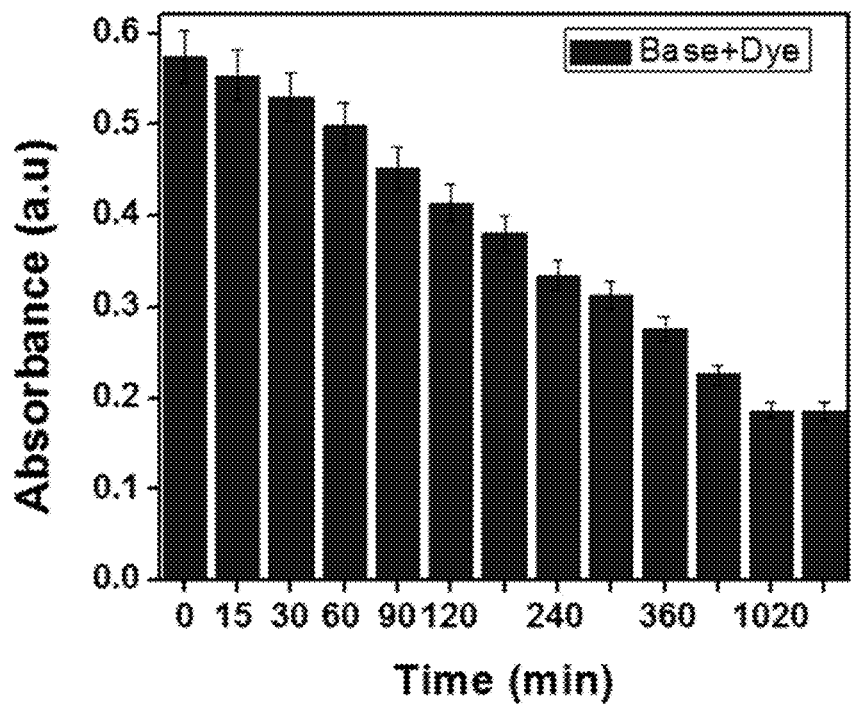
FIG. 16 shows the absorbance pattern of DiI dye in a base cream in the presence of UV light over time, which shows there is much change in the absorbance of the DiI dye in the base cream over time that indicates the protective nature of base cream to the dye thereby mimicking the protection of skin from UV light afforded by the base cream.

C. Stability of Base and DiI Dye Together as One Solution in the Presence of UV-Light A homogenized solution of base and DiI dye was prepared and checked for the stability in the presence of UV light (UVA: 315-400 nm and UVB: 280-315 nm). This shows that the PEG-SBO polymer protect the DiI from quenching in the presence of UV light. The base and DiI dye solution was exposed to the UV source for 24 h and data was collected in a timely pattern. As shown in FIG. 16, the dye was not easily quenched. It was found to be stable until 6 h of time and this effect is due to the PEG-SBO polymer. The results indicate that the PEG-SBO polymer protected the dye from quenching by UV light. Thus, a lotion formulated with PEG-SBO polymer will be able to protect human skin from harmful UV rays of sun.

Figure 17:
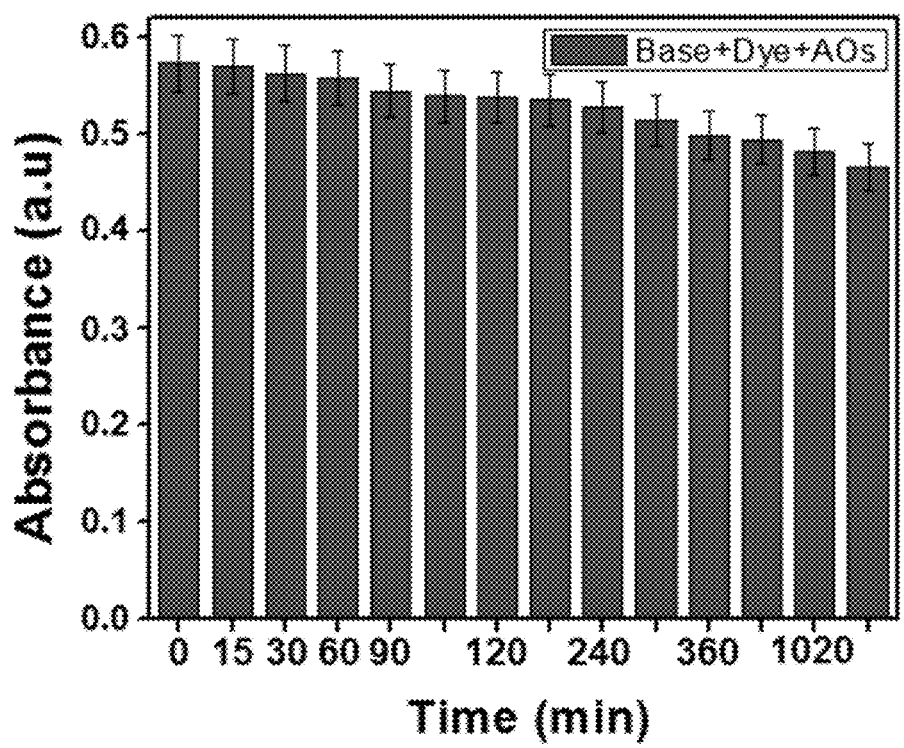
FIG. 17 shows the absorbance pattern of DiI dye and the soybean antioxidants in a base cream in the presence of UV light over time, which shows there is little change in the absorbance of the mixture over time that indicates the antioxidants provide substantial improvement in the protective nature of base cream to UV light.

D. Stability of Base, DiI Dye and Soybean Antioxidants (Genistein and Daidzein) Together in Solution in the Presence of UV-Light Homogenized solution of base, DiI dye and soybean-antioxidants was prepared and checked for the stability in the presence of UV light (UVA: 315-400 nm and UVB: 280-315 nm). As described above, the base is protecting DiI from quenching to a good extent. But in this sample, the activity of soybean antioxidants in protection of DiI from quenching in UV light was evaluated. For that, the solution of base, DiI dye and soybean antioxidants was exposed to the UV source for 24 h and data was collected in a timely pattern. As shown in FIG. 17, the dye was more protected than that of presence of base alone. It was found to be stable until 6 h of time and this effect is due to the PEG-SBO polymer. The results indicate that the PEG-SBO polymer protects the dye from quenching by UV light.

Figure 18:
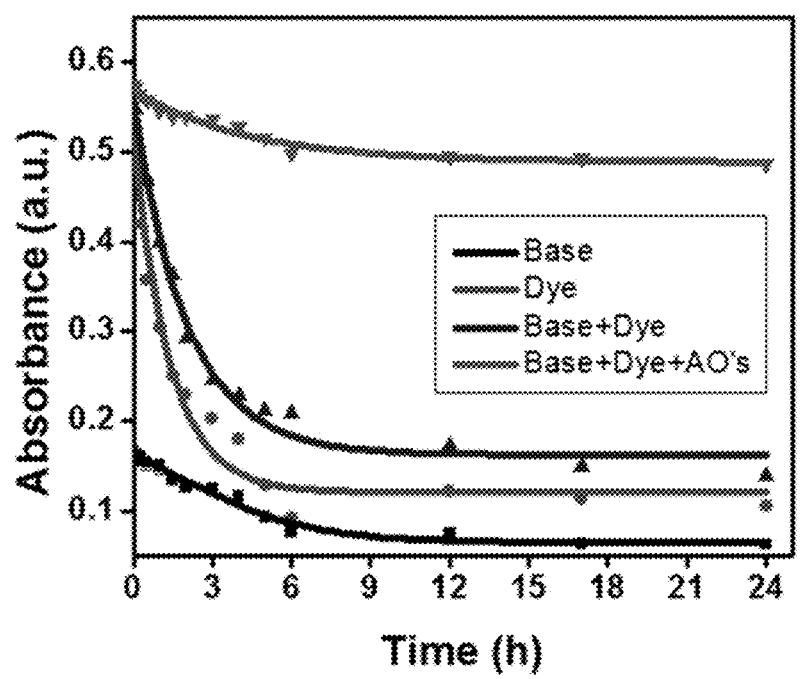
FIG. 18 is a comparison of the absorbance patterns of the base cream, DiI dye, and soybean antioxidants in the UV light.

Also, FIG. 18 provides a comparison of absorbance pattern of base, DiI dye and soybean antioxidants in the presence of UV light. As shown, antioxidants and base together are showing good protective nature against DiI quenching.

Example IV

A. Formulation of Lotion

1. Materials

The PEG-SBO polymer included as the Active Pharmaceutical Ingredient (API); Hexadecanol included for the consistency factor; Isopropyl Myristate included as an emollient; Polysorbate 60 included as an emulsifier; Genistein included as a soybean-derived antioxidant; Daidzein included as a soybean-derived antioxidant; Glycerol included as a humectant; water included as a solvent; nanoceria included as antioxidant; herbal extract as anticancer agent; lavender oil as fragrance; rose water as fragrance.

2. Preparation of Topical Lotions

Five formulations F1, F2, F3, F4 and F5 (i.e., Shifa lotion, Shifa Nanoceria (Shifa NC), Herbal lotion, Herbal Nanoceria (Herbal NC) and Nanoceria lotion (NC), respectively) were prepared. Phase I ingredients (Oil Phase) and Phase II ingredients (Aqueous Phase). Stirring was continued until a smooth and uniform paste was obtained. Cool down to 30° C. with continuous stirring and if needed an ice bath.

B. Determination of Physicochemical Parameters

1. Determination of Organoleptic Acceptability

The color and odor of the prepared lotions and commercial lotions (i.e., AVEENO and BANANA BOAT lotions) were visibly observed for their organoleptic acceptability.

Color of the prepared lotions were found to be creamy white. No change in the color of formulation was observed even over multiple days. The prepared lotions were characterized with aromatic odor and pleasant smell due to fragrance and perfume added.

2. Phase Separation and Centrifugation Test

The formulation was analyzed for stability under different storage conditions to note the effect of these conditions on storage capability of lotion. The samples were placed at −80° C., −20° C., 4° C., and 37° C. then tested for phase separation and breakage on centrifugation. The formulations showed no phase separation when placed at −80°, −20°, 4°, and 37° C., which indicated that the prepared lotions were relatively more stable at all temperatures. Also, no phase separation on centrifugation was seen in any of the samples 7. Determination of pH 1 gm of lotion was dissolved in 100 ml of distilled water and pH of formulations was measured using digital pH meter.

As shown in Table 1 below, the prepared lotions are comparable with marketed lotions confirming the stability and efficacy of our lotions with that of marketed lotions.

TABLE 1

| Formulations/Parameters | Shifa lotion | Shifa lotion with NC | Aveeno lotion | Banana Boat lotion | Herbal lotion | Herbal NC lotion | NC lotion |
|---|---|---|---|---|---|---|---|
| Color | Creamy | Creamy | Creamy White | White | Light green | Light green | White |
| Odor | Pleasant | Pleasant | Pleasant | Aromatic | Pleasant | Pleasant | Pleasant |
| pH | 6.2 | 6.3 | 7.05 | 7.14 | 6.9 | 7.02 | 6.8 |
| Centrifugation test | No breakage | No breakage | No breakage | No breakage | No breakage | No breakage | No breakage |
| Spreadability (sec) | Easily spreadable | Easily spreadable | Easily spreadable | Easily spreadable | Easily spreadable | Easily spreadable | Easily spreadable |
| Phase separation | No phase separation | No phase separation | No phase separation | No phase separation | No phase separation | No phase separation | No phase separation |
| Viscosity (Pa · s) | 1.27 | 1.25 | 0.9062 | 0.9110 | 1.062 | 1.198 | 2.675 |
| SPF | 35 | 36 | 30 | 30 | 33 | 43 | 32 | kept under different storage conditions mentioned above indicating that the formulations were stable at all storage conditions.

3. Determination of Sedimentation Volume and Re-Dispersibility

The prepared formulations along with commercial lotions were tested for sedimentation volume. The sample was homogenized uniformly with water and kept aside and observed for the sedimentation rate. After sedimentation, the emulsion or suspension is re-dispersed by mixing and noted for re-dispersibility of the formulation.

No sedimentation was observed for the prepared lotions. It was uniformly distributed throughout the solution and there was no separation of the particles. Yet, when re-dispersed they were easily mixed. This shows that the prepared lotions were stable uniformly homogenized.

4. Determination of pH

The pH of formulation ranges from 6.2 (F1) to 7.02 (F4) in comparison to pH 7 of the commercial lotions. All the lotion formulations were within 6.2-7 range and compatible with typical skin pH of about 5.5.

5. Determination of Viscosity

Viscosity of lotion was measured by AR 2000 ex from TA instrument. The test conditions were maintained at 25° C. using a 2° steel cone parallel plate viscometer. The gap setting between the plates was set to 55 mm. The condition maintained was continuous ramp of flow procedure with shear rate 2.864-286.4. The experiment was conducted thrice and the average viscosity of the lotions were reported.

Figure 22:
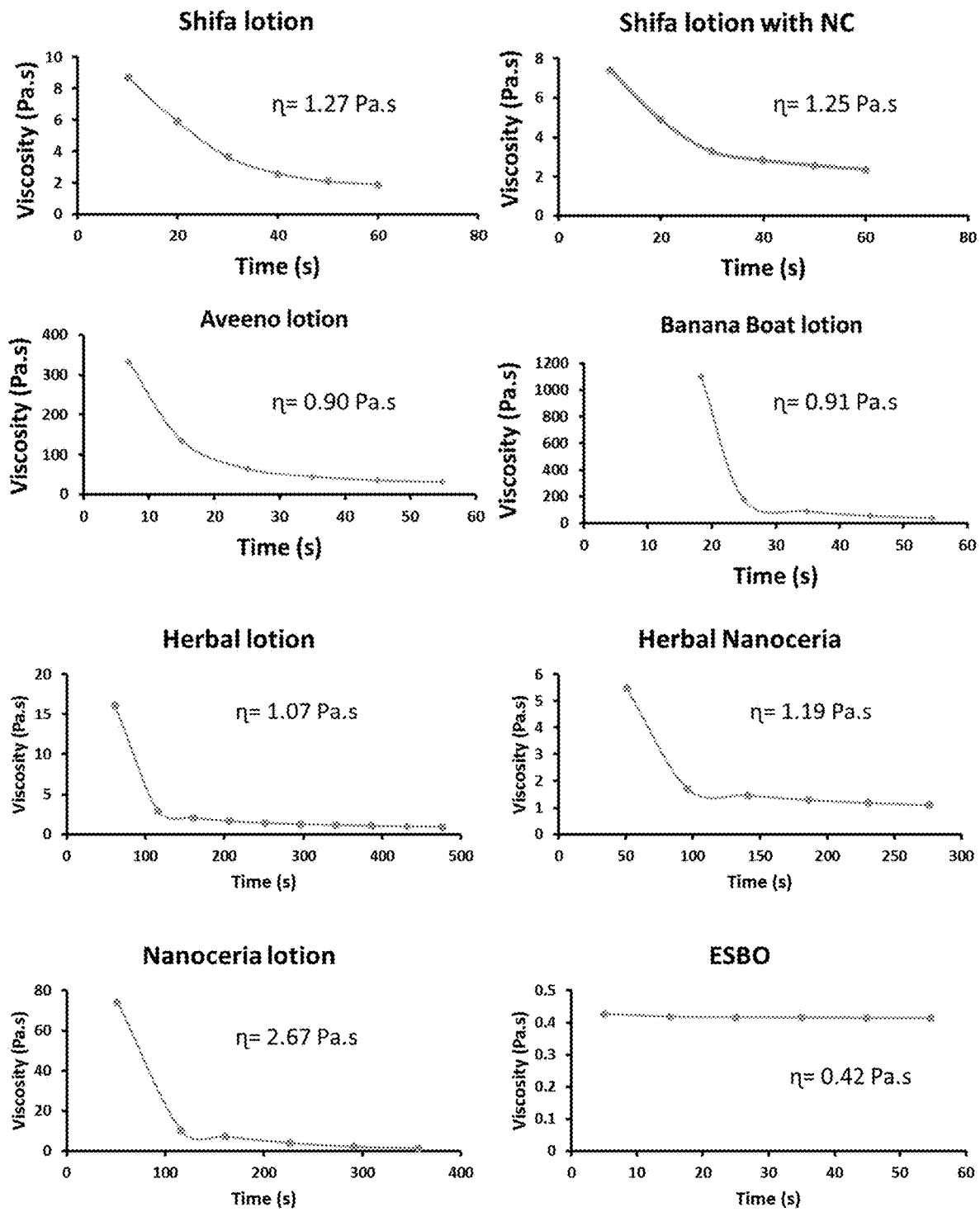
FIG. 22 are graphs of viscosity versus time of the identified lotions.

Viscosity of the prepared formulations ranges from 1.27 to 2.67 Pa·S comparable to the commercial lotions with an average of 0.91 Pa·S. The spreadability of the formulation ranges from 2.5 to 9.56 g·cm/sec (see FIG. 22).

6. Determination of Spreadability

Spreadability refers to the ease with which product can be spread without losing its firmness. It is determined based on "Slip" and "Drag" characteristics of a lotion. An excess of lotion (about 10 g) was positioned on fixed slide and sandwiched using another glass slide to impart uniform film of lotion between slides. The ease at which the lotion is spread is observed and the time is noted. A shorter time interval indicated better spreadability.

C. Rheological Studies

Different experimental procedures were followed for different rheological studies. Dynamic experiments are performed with a shear stress sweep from 0.5968 to 59.68 and oscillatory conditions are maintained with a frequency sweep of 1 to 100.

1. Oscillatory Conditions

The formulation was tested for various rheological studies under oscillatory, creep and dynamic conditions. The results in FIG. 23 were obtained when the lotions were exposed to small cyclic (oscillatory) stress. Oscillatory experiments are particularly useful as non-destructive method for determining the structure of delicate materials over short and medium periods of time. These tests define the elastic nature of the lotion.

Figure 23:
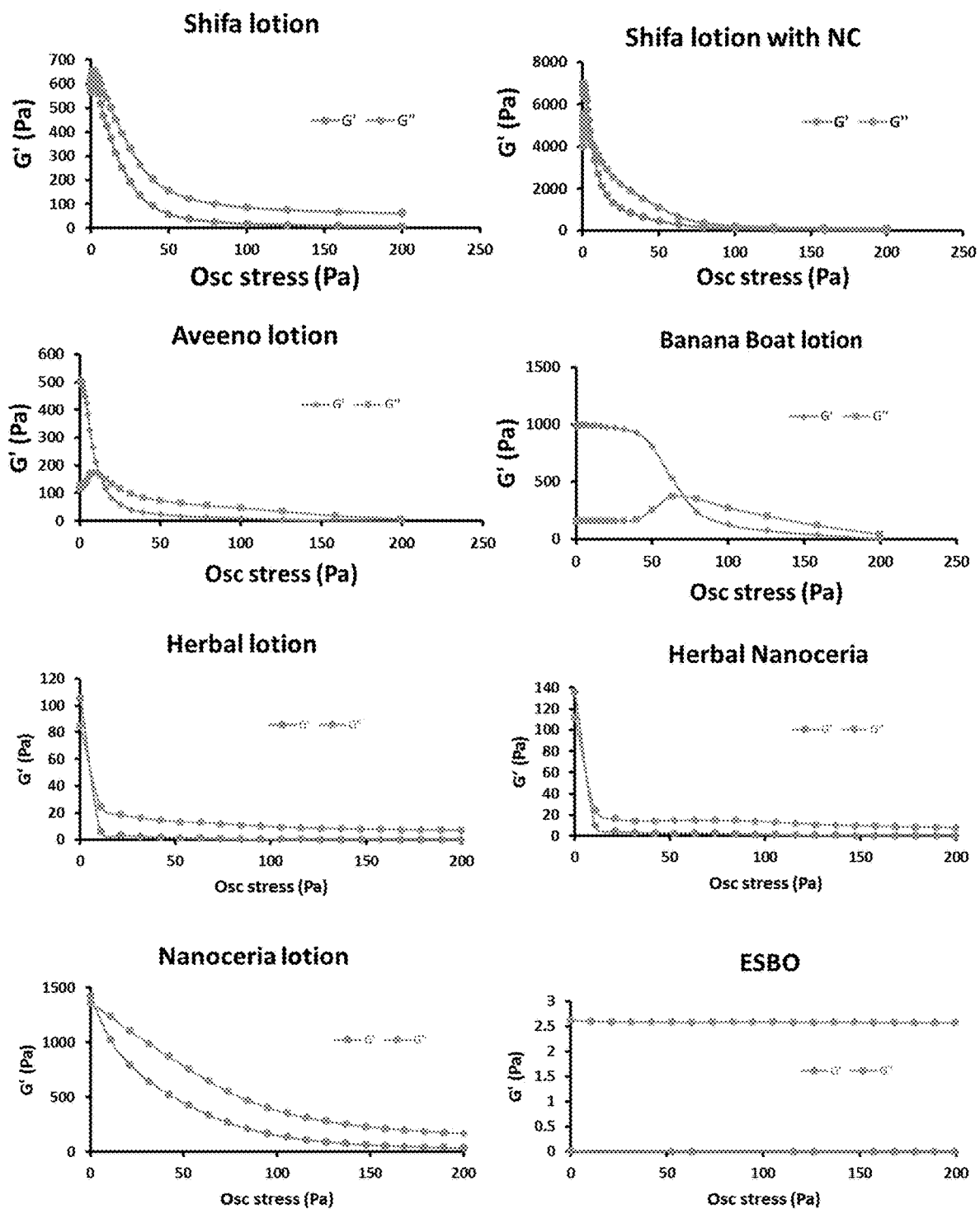
FIG. 23 are graphs depicting the behaviors of the identified lotions when subjected to small oscillatory stress.

The basic principle of an oscillatory rheometer is to induce a sinusoidal shear deformation in the sample and measure the resultant stress response; the time scale probed is determined by the frequency of oscillation, $\omega$, of the shear deformation. Viscoelastic materials show a response that contains both in-phase and out-of-phase contributions. The viscoelastic behavior of the system at w is characterized by the storage modulus, $G'(\omega)$, and the loss modulus, $G''(\omega)$, which respectively characterize the solid-like and fluid like contributions to the measured stress response. For a sinusoidal strain deformation $\gamma(t)=\gamma_0 \sin(\omega t)$, the stress response of a viscoelastic material is given by $\sigma(t)=G'(\omega)\gamma_0 \sin(\omega t)+G''(\omega)\gamma_0 \cos(\omega t)$. In a typical rheological experiment, $G'(\omega)$ and $G''(\omega)$ are measured. The measurements are a function of omega because whether a soft material is solid-like or liquid-like depends on the time scale at which it is deformed. As shown in FIG. 23, $G'(\omega)$ and $G''(\omega)$ are plotted for each lotion suspension; at the lowest accessible frequencies, the response is viscous-like, with a loss modulus that is much larger than the storage modulus while at the highest frequencies accessed the storage modulus dominates the response, indicating solid-like behavior.

2. Dynamic Conditions

The dynamic (shear) viscosity of a fluid expresses its resistance to shearing flows, where adjacent layers move parallel to each other with different speeds. Fluids resist the relative motion of immersed objects through them as well as to the motion of layers with differing velocities within them.

Viscosity (represented by the symbol η "eta") is the ratio of the shearing stress (F/A) to the velocity gradient ($\Delta v_x/\Delta z$ or $dv_x/dz$) in a fluid.

$$\eta = (F/A)/\Delta v_x/\Delta z$$

Figure 24:
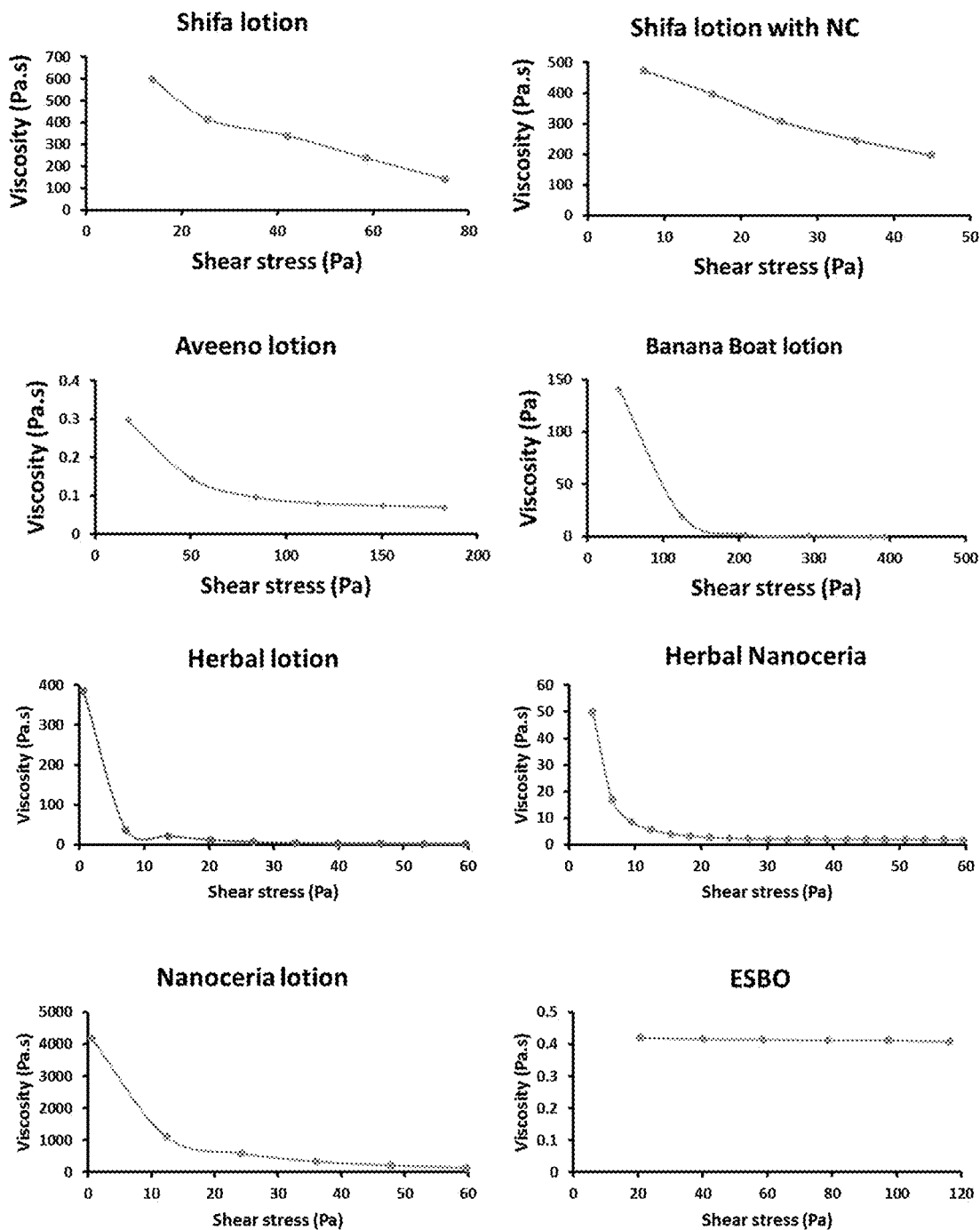
FIG. 24 are graphs depicting the behaviors of the identified lotions when subjected to shear stress.

The results of the flow test under dynamic conditions indicates the apparent yield stress and viscosity of the formulation prepared. All the results indicate higher apparent yield stress under comparable conditions. Of particular interest, the high shear stress region of FIG. 24 are believed to approach conditions at which a lotion would see while rubbing the surface. The FIG. 24 data show apparent yield stress and good viscous properties. The viscosity of the all formulated lotions is higher than the commercial lotions.

D. Antioxidant Assay

1. Hydrogen Peroxide Scavenging Assay

Hydrogen peroxide scavenging of the formulations was determined according to the method of Ebrahimzadeh et al., *Antioxidant Activity of the Bulb and Aerial Parts of Ornithogalum sintenisii* L (Liliaceae) at *Flowering Stage*, Tropical J Pharmal Res. 2010a, 9, 2, 141-148. One ml of formulation was added to 2 ml of hydrogen peroxide solution (10 mM) in phosphate buffer (50 mM, pH 7.4). The sample was replaced by methanol for control. Reaction mixture was incubated at room temperature for 30 min. The unreacted hydrogen peroxide was determined by measuring the absorbance of the reaction mixture at 230 nm with respect to the blank (methanol) using UV/visible spectrophotometer. The percentage inhibition was calculated according to the following equation:

$$\text{Percentage inhibition} (\%) = \frac{A control - A sample}{A control} \times 100$$

wherein Acontrol is the absorbance of control and Asample is the absorbance of the sample. The hydrogen peroxide scavenging activity of the lotions is set forth in Table 2 below, wherein the % Inhibition shows the amount of hydrogen peroxide that is inhibited by the sample.

TABLE 2

| Formulation | % Inhibition in methanol | % Inhibition in Water |
|---|---|---|
| Shifa lotion | 53.52 | 67.8 |
| Shifa NC lotion | 83.11 | 86.13 |
| Aveeno lotion | 53.32 | 67.37 |
| Banana Boat lotion | 52.29 | 61.19 |
| Herbal lotion | 59.28 | 42.90 |
| Herbal NC lotion | 66.41 | 67.77 |
| Nanoceria lotion | 54.35 | 33.26 |

Figure 25:
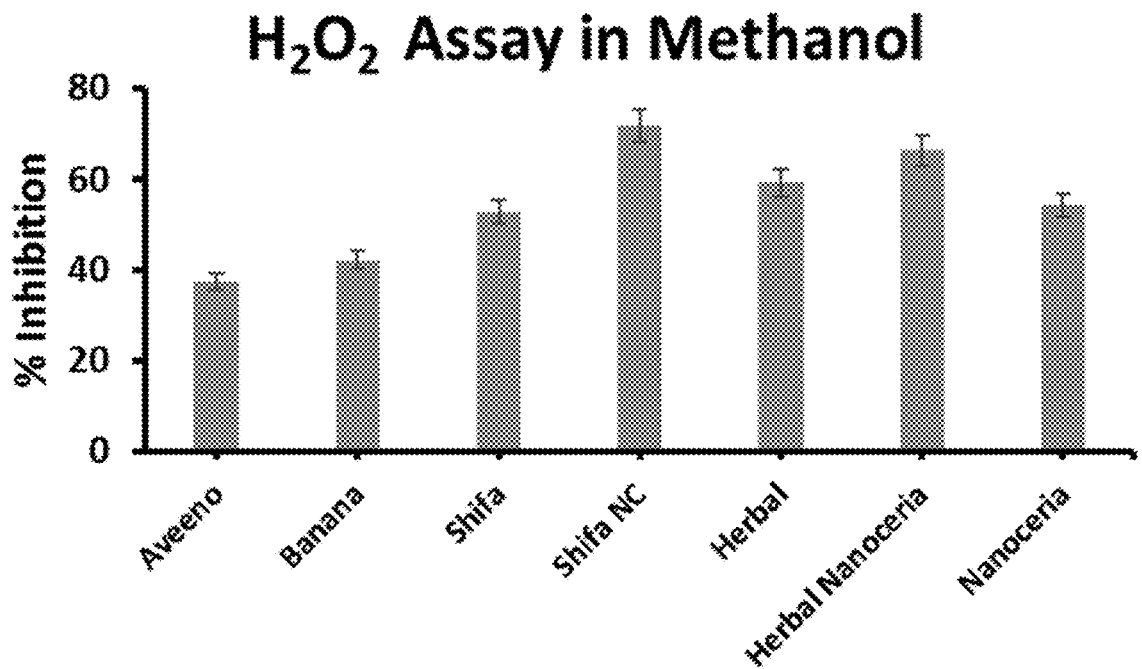
FIGS. 25A and B are graphs of the % inhibition of hydrogen peroxide in two different solvents, methanol and water, of the identified lotions.
Figure 25:
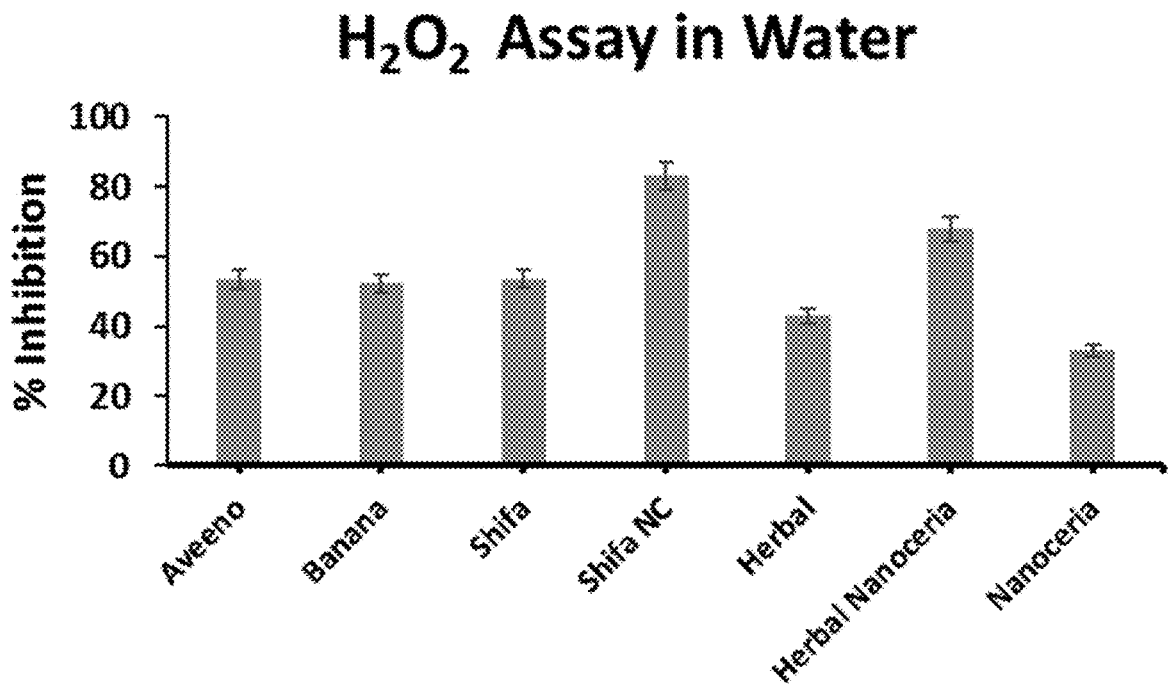
Figure 26:
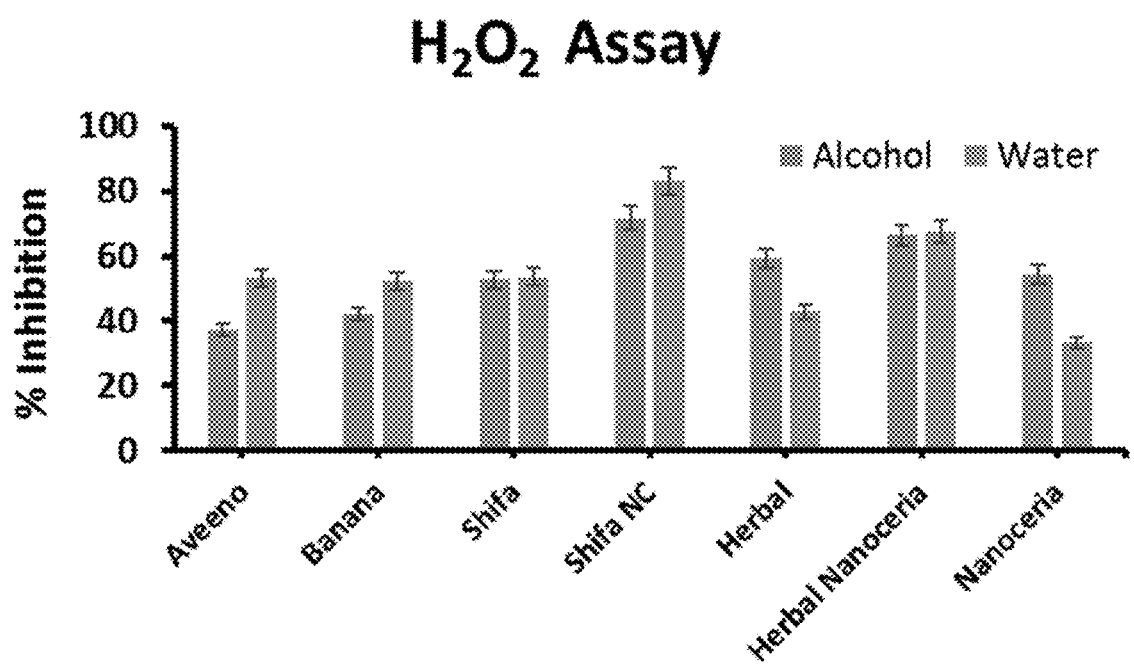
FIG. 26 is a graph comparing the % inhibition of $H_2O_2$ in two different solvents of the identified lotions.

The experiment was conducted in two different solvents and as shown in FIGS. 25A and B and 26, there was comparable antioxidant activity for both solvents. Shifa Nanoceria showed a markedly higher antioxidant activity of scavenging hydrogen peroxide when compared to the other formulations.

2. DPPH (2, 3-Diphenyl-1-Picrylhydrazyl) Radical Scavenging Assay

The DPPH free radical scavenging capability of prepared lotions was performed as the method described by Braca et al., *Antioxidant principles from Bauhinia terapotensis*, J. Nat. Prod., 2001, 64, 892-895, with slight modifications. One milliliter of lotion dissolved in methanol was added to 3 ml of 0.1 mM methanolic solution of DPPH. Sample volume was replaced by methanol and used as control. Reaction mixture was incubated in dark room at room temperature for 30 minutes. The Absorbance of the reaction mixture was measured at 517 nm using UV/Visible spectrophotometer. The percentage inhibition of DPPH radical was calculated according to the following equation:

$$\text{Percentage inhibition} (\%) = \frac{A control - A sample}{A control} \times 100$$

wherein Acontrol is the absorbance of control and Asample is the absorbance of the sample. The DPPH scavenging activity of the lotions is set forth in Table 3 below, wherein the % Inhibition shows the amount of DPPH that is inhibited by the sample.

TABLE 3

| Formulation | % Inhibition in methanol | % Inhibition in Water |
|---|---|---|
| Shifa lotion | 66.19 | 53.52 |
| Shifa NC lotion | 82.30 | 83.11 |
| Aveeno lotion | 56.49 | 53.32 |
| Banana Boat lotion | 60.94 | 52.29 |
| Herbal lotion | 72.69 | 62.08 |
| Herbal NC lotion | 83.45 | 76.62 |
| Nanoceria lotion | 60.15 | 54.44 |

Figure 27:
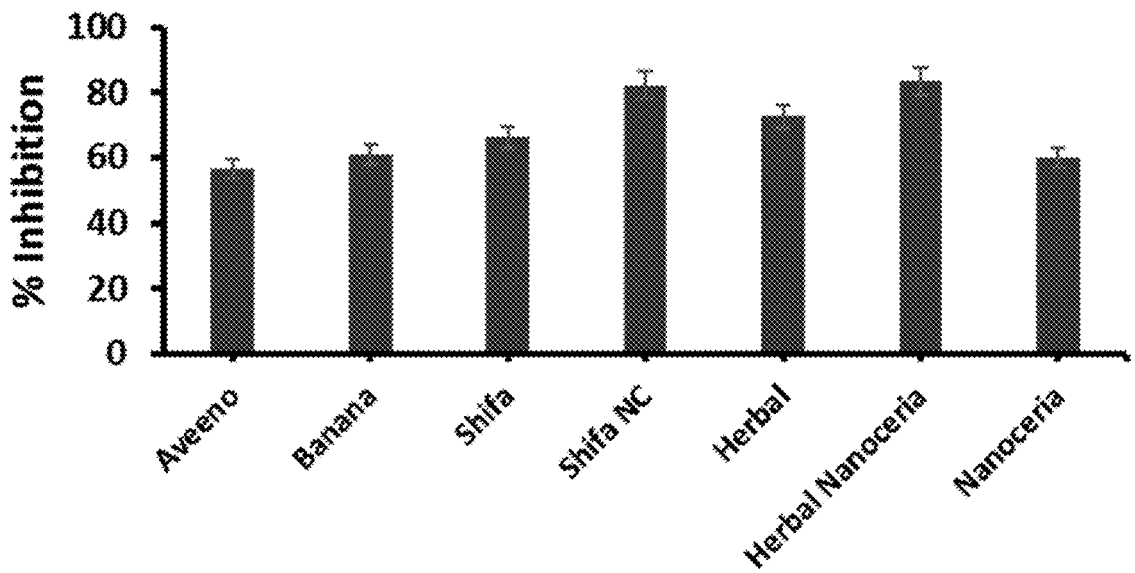
FIGS. 27A and B are graphs of the % inhibition of DPPH in two different solvents, methanol and water, of the identified lotions.
Figure 27:
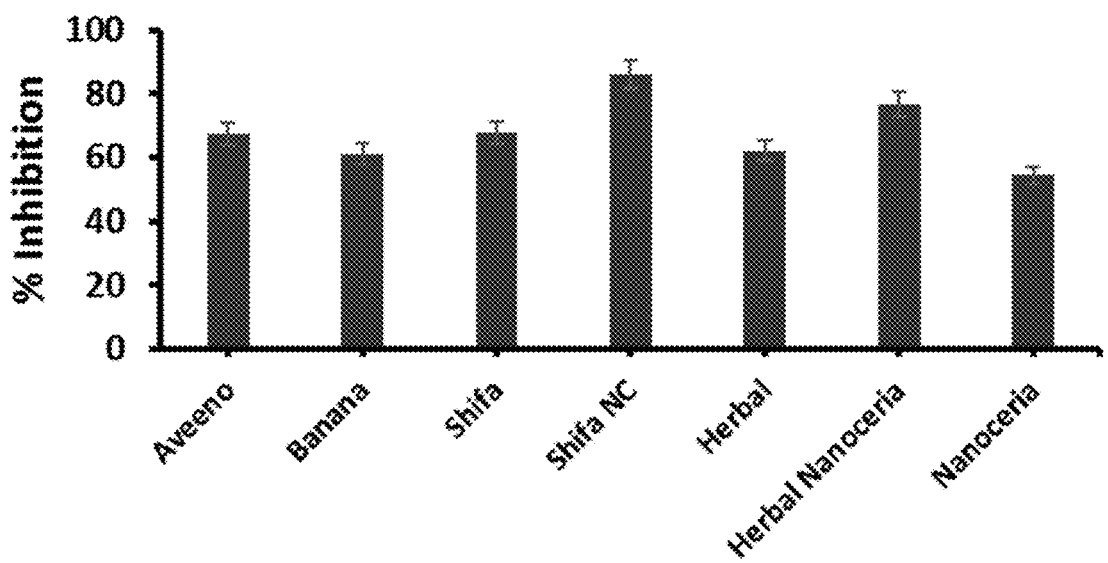
Figure 28:
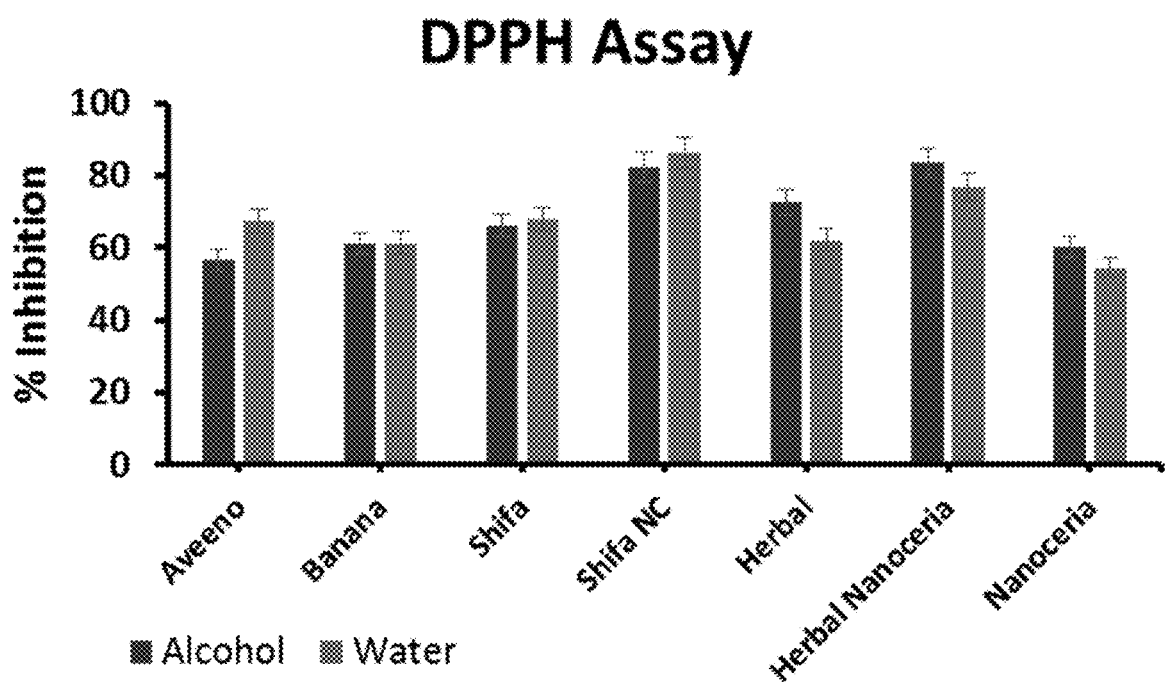
FIG. 28 is a graph comparing the % inhibition of DPPH in two different solvents of the identified lotions.

The experiment was conducted in two different solvents and as shown in FIGS. 27A and B and 28, there was comparable antioxidant activity for both solvents. The Shifa NC and Herbal NC lotions had high DPPH radical scavenging assay when compared with other formulations.

E. Thermogravimetric Analysis (TGA)

Thermogravimetric analysis or thermal gravimetric analysis (TGA) is a method of thermal analysis in which changes in physical and chemical properties of materials are measured as a function of increasing temperature (with constant heating rate), or as a function of time (with constant temperature). TGA is commonly used to determine selected characteristics of materials that exhibit either mass loss or gain due to decomposition, oxidation, or loss of volatiles (such as moisture). Thermogravimetric analysis (TGA) relies on a high degree of precision in three measurements: mass change, temperature, and temperature change. Therefore, the basic instrumental requirements for TGA are a precision balance with a pan loaded with the sample, and a programmable furnace. The furnace can be programmed either for a constant heating rate, or for heating to acquire a constant mass loss with time.

Figure 29:
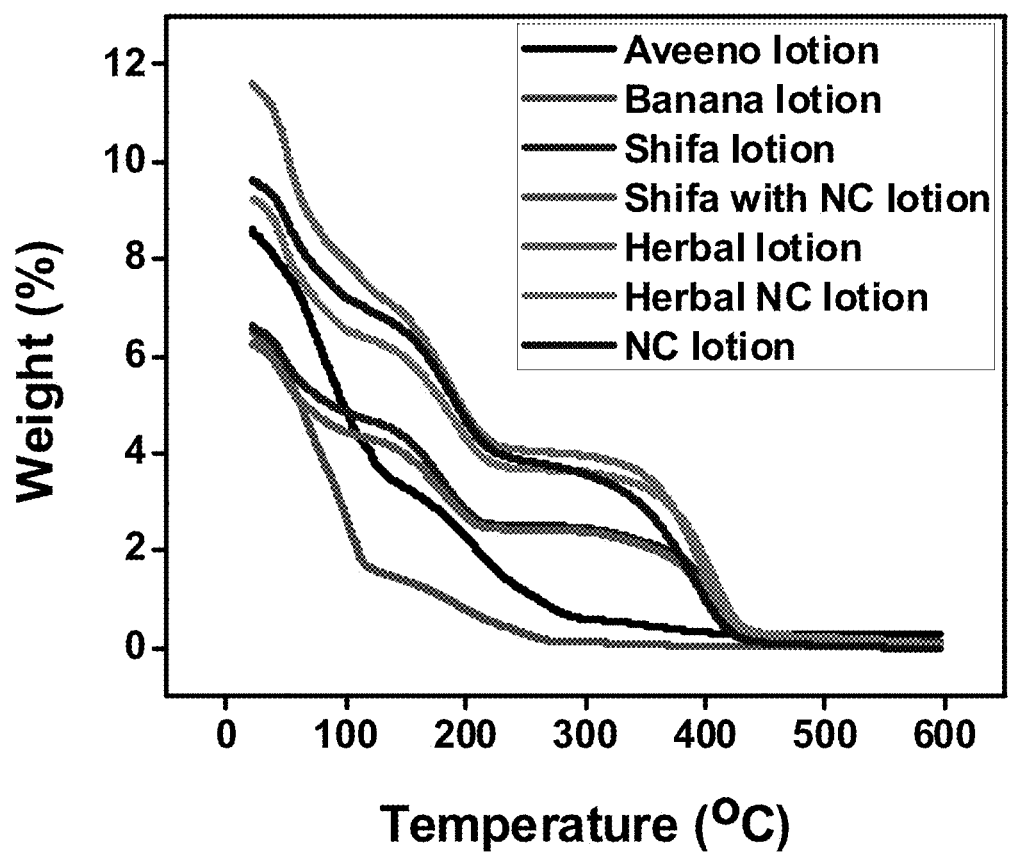
FIG. 29 is Comparative TGA Curves of the identified lotions, wherein all the prepared lotions exhibit a hump between 300-400° C. indicating the stability of lotions through this temperature range compared to commercially available lotions.

Comparative graphs of TGA in FIG. 29 show a hump for formulated lotions between 300-400° C. indicating that they are more stable than the commercial lotions.

F. Differential Scanning calorimetry (DSC) Thermal Analysis

DSC is used to measure melting temperature, heat of fusion, latent heat of melting, reaction energy and temperature, glass transition temperature, crystalline phase transition temperature and energy, precipitation energy and temperature, denaturation temperatures, oxidation induction times, and specific heat or heat capacity. DSC measures the amount of energy absorbed or released by a sample when it is heated or cooled, providing quantitative and qualitative data on endothermic (heat absorption) and exothermic (heat evolution) processes.

The output yielded by differential scanning calorimetry is called a differential thermogram, which plots the required heat flow against temperature. Data analysis is highly dependent on the assumption that both the reference and sample cells are constantly and accurately maintained at equal temperatures. The DSC graph indicates the change in power (electrical heat) as the temperatures of the two cells are gradually increased. A change in specific heat results in a small change in power, and can be either positive or negative depending on the particular process. The advent of an endothermic reaction will cause an increase in power as temperature increases, since additional heat is required to drive the reaction and still maintain the reference temperature. When an exothermic reaction occurs, the opposite effect is observed; power decreases because heat is released by the reaction and less power is required to maintain equivalent temperatures in the chambers.

Figure 30:
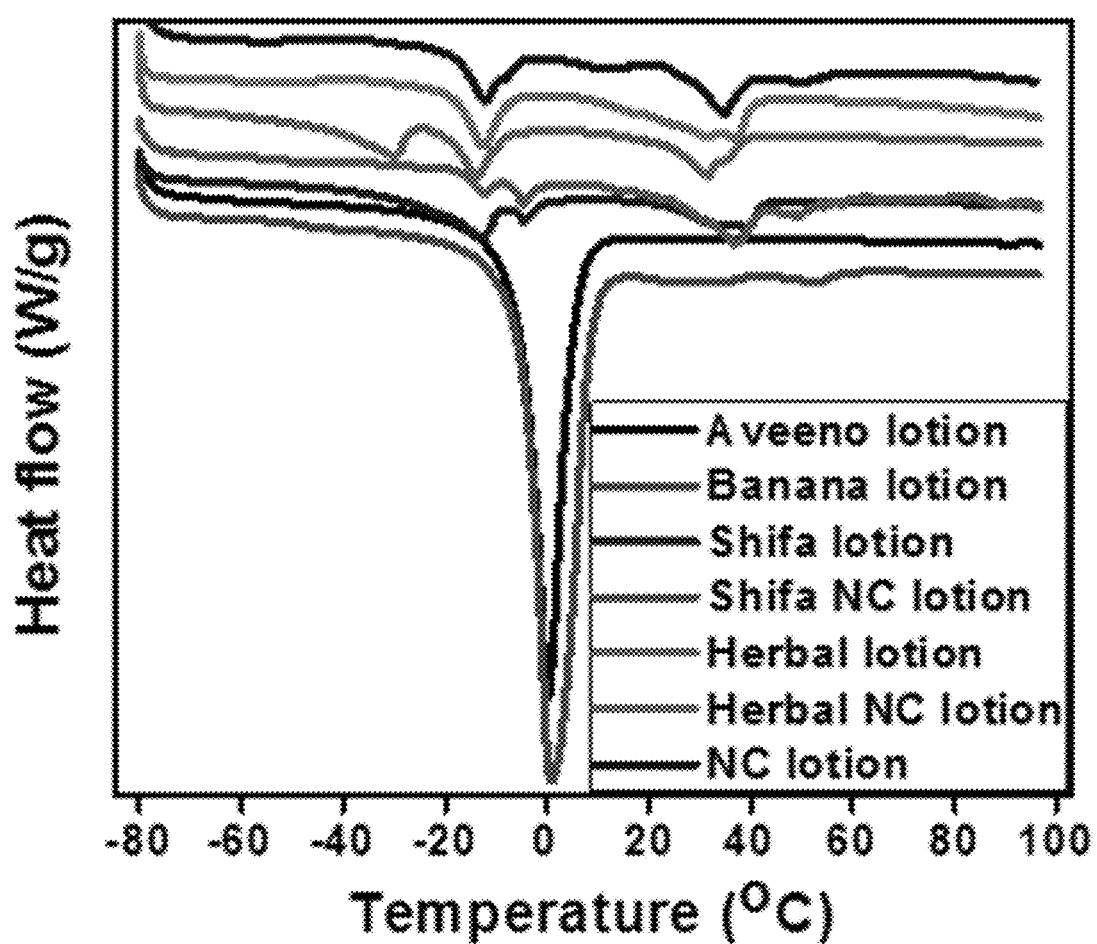
FIG. 30 is DSC graphs of the identified lotions; the commercially available lotions have a deep exothermic peak.

FIG. 30 contains DSC graphs of the prepared and commercial lotions are represented. The commercial lotions have significantly deeper exothermic peaks.

G. FTIR Spectroscopic Studies

FTIR stands for Fourier transform infrared, the preferred method of infrared spectroscopy. When IR radiation is passed through a sample, some radiation is absorbed by the sample and some passes through (is transmitted). The resulting signal at the detector is a spectrum representing a molecular "fingerprint" of the sample. The usefulness of infrared spectroscopy arises because different chemical structures (molecules) produce different spectral fingerprints. The FTIR uses interferometry to record information about a material placed in the IR beam. The Fourier Transform results in spectra that analysts can use to identify or quantify the material.

Figure 31:
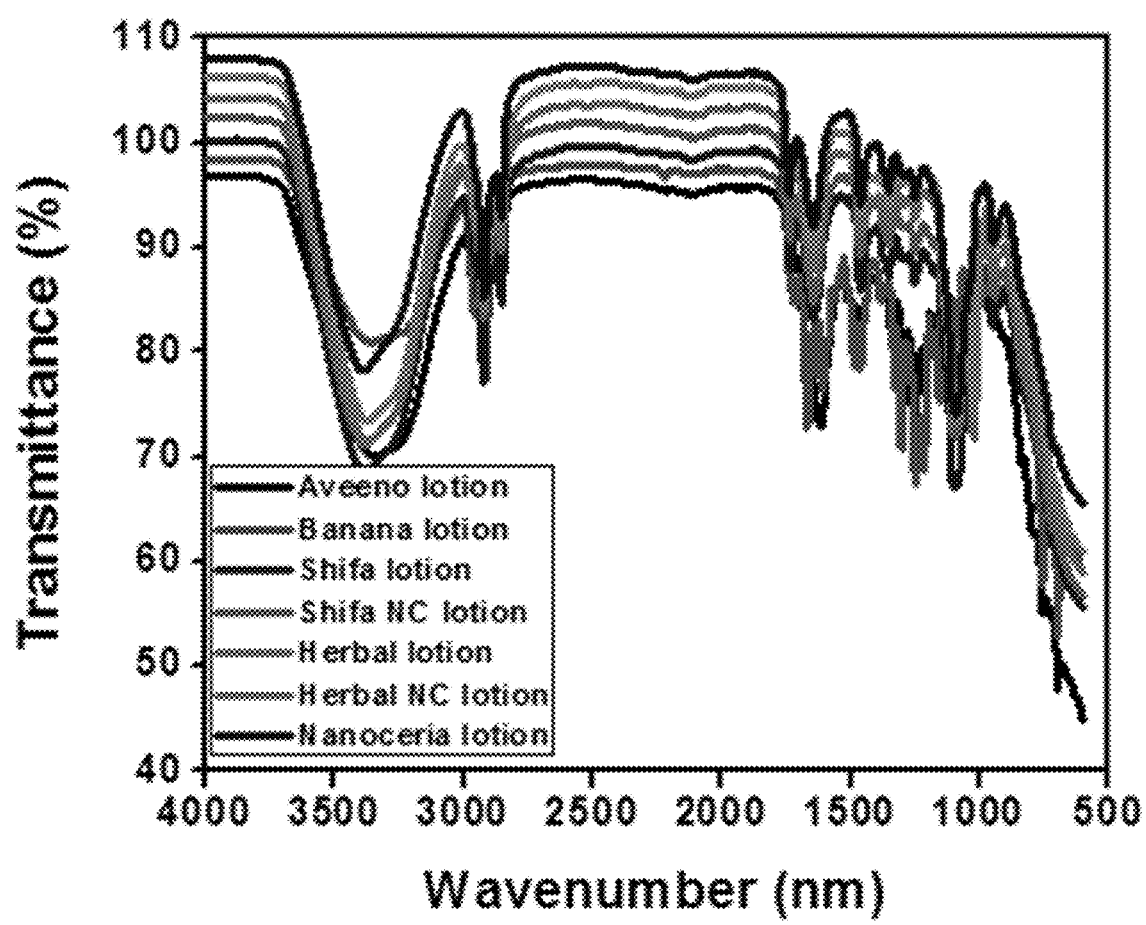
FIG. 31 is FT-IR spectroscopy of the identified lotions; the hump at the 3200 nm wavelength indicates the pronounced OH groups due to the presence of PEG molecules.

Referring to FIG. 31, the hump at the 3200 nm wavelength in formulated lotions indicates the pronounced OH groups due to the presence of PEG molecules. All the functional groups of formulated lotions performed like the commercial lotions. The broad at about 3200 cm$^{-1}$ is an indication of presence of hydroxyl groups. The peak of the formulated lotions is due to PEG.

H. UV-Light Protection Study of Lotions

1. Stability in the Presence of UV-Light

Figure 32:
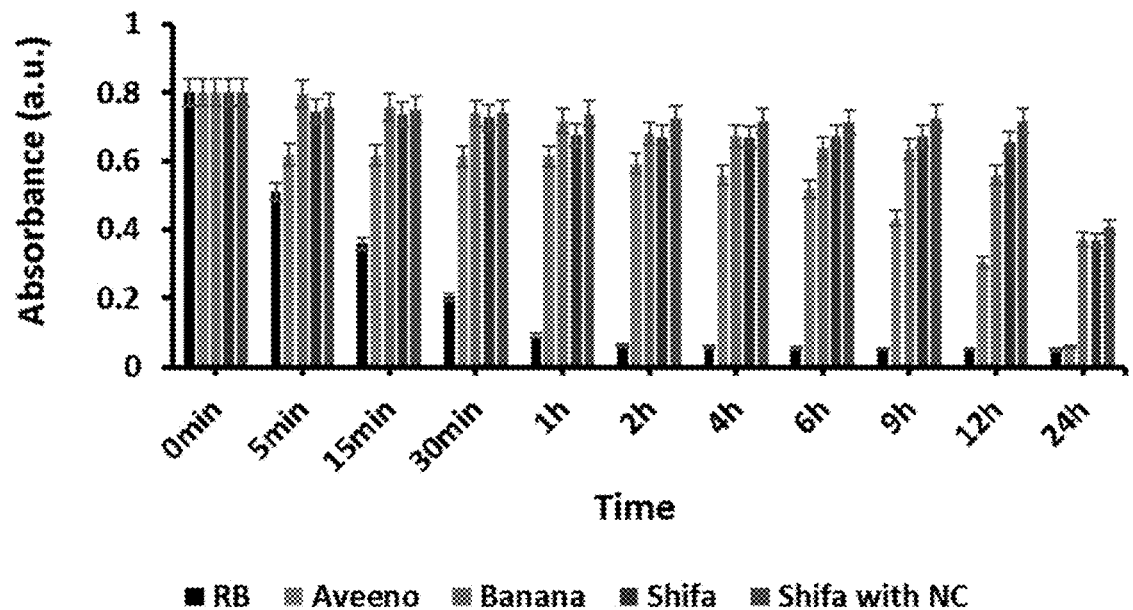
FIGS. 32A and B are graphs comparing the absorbance of the identified lotions in the presence of Rose Bengal dye, which shows the prepared lotions are more protective and stable against dye quenching than the commercially available lotions.
Figure 32:
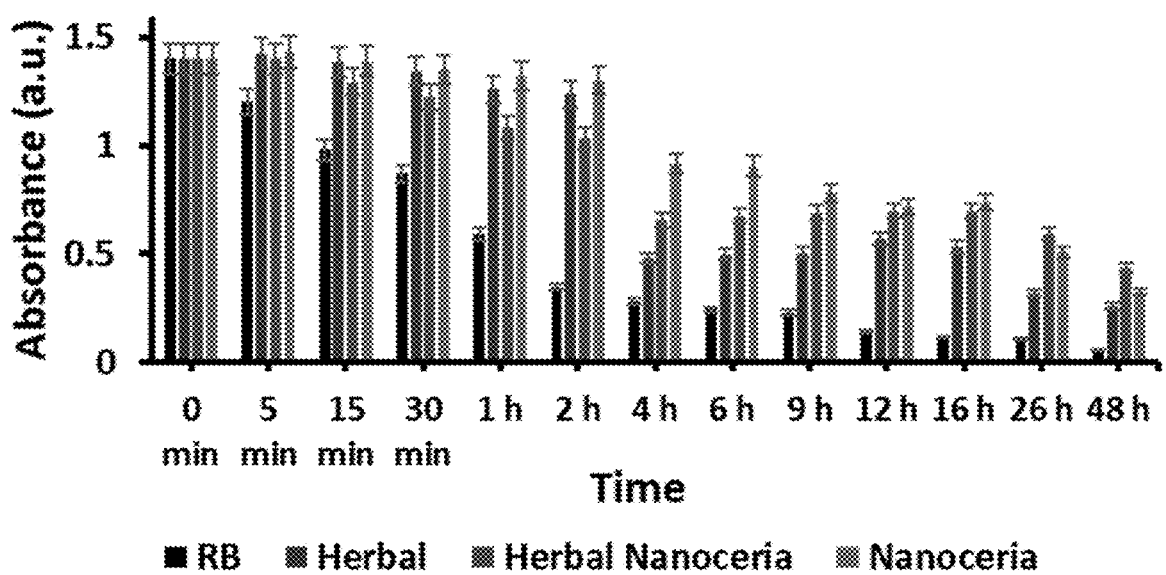
Figure 33:
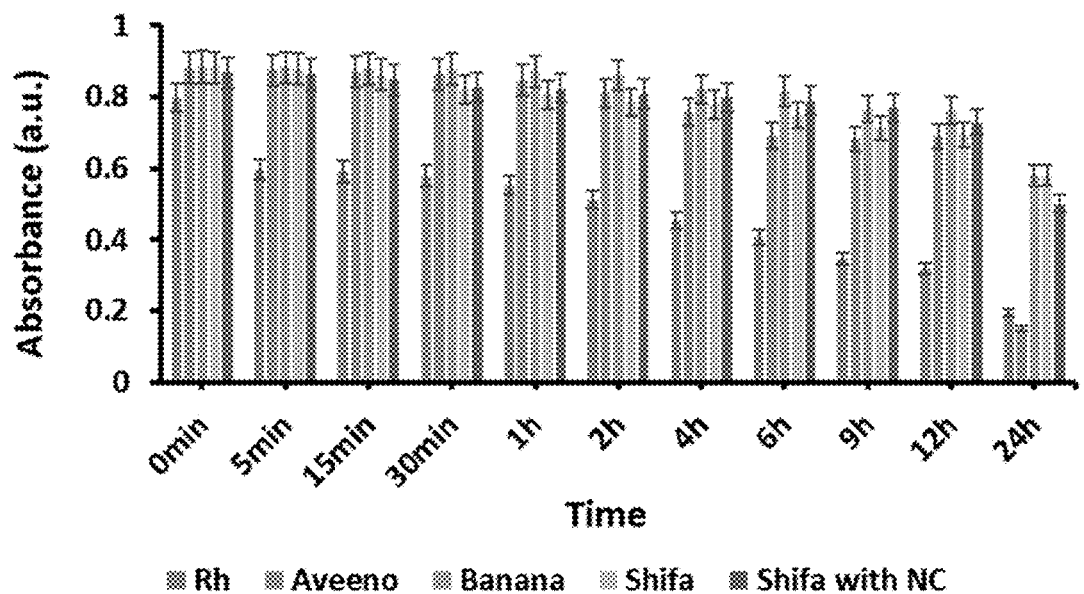
FIGS. 33A and B are graphs comparing the absorbance of the identified lotions in the presence of Rhodamine dye, which shows the prepared lotions are more protective and stable against dye quenching than the commercially available lotions.
Figure 33:
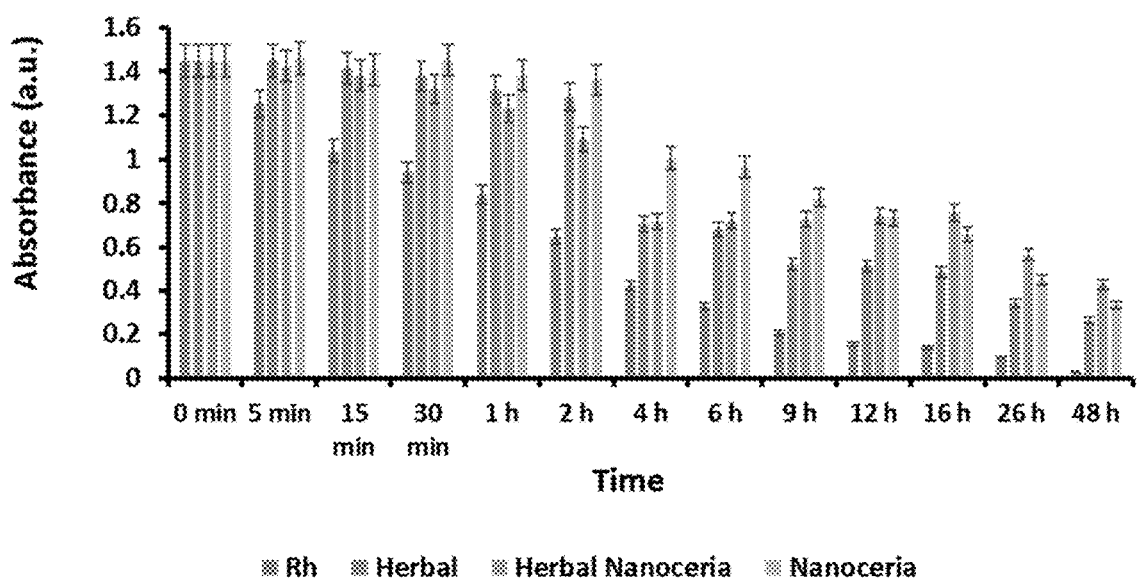

The UV stability of the lotions were tested using dye (Rose Bengal Dye, RB) in the presence of UV light (UVA: 315-400 nm and UVB: 280-315 nm). The lotions were exposed to the UV source for 24 h. As shown in FIGS. 32A and B, the dye is quenched very rapidly in the presence of UV light. About 80% of dye was quenched within 2 hours. This indicated that dye is not UV-resistant and is a good representation of the sensitivity of human skin to sun rays. The prepared lotions with antioxidants and base (PEG-Polymer) and commercial lotions in presence of Rose Bengal dye stabilized the dye against the UV radiation. As shown in FIGS. 32A and B, when compared with commercial lotions, the formulated lotions were more stable and prevented the dye from being quench for longer exposures. Thus, the prepared lotions are more stable with less active ingredients and are capable of inhibiting UV rays from sun preventing skin burns and skin cancer.

2. UV Absorption Protection Studies with Rhodamine Dye

To further confirm the stability of the prepared lotions, the UV protection using another dye called Rhodamine (Rh) was evaluated. The dye, without the protection afforded by a lotion, was easily quenched but the lotions stabilized the dye against UV for long periods, which indicated that the base ingredient (i.e., the PEG-polymer base) inhibits the absorption of sun rays into the skin.

3. Determination of Sun Protection Factor (SPF)

The exposure of UV solar radiation to human body fabricates harmful effects on the skin, including sunburn, photoaging, cutaneous malignancies, local immunosuppression and damage DNA. People protect themselves by clothes, hats, scarves, etc. The sun's rays continuously reach to earth with approximately 50% visible light, 40% infrared radiation, and 10% UV radiation. The UV A wavelengths (320-400 nm) are contributed significantly to photoaging because they travel deeper into the skin than the visible and infrared. The shorter wavelengths (UV B) are 30-40 times more energetic, and penetrate mostly into the epidermis. Further this may lead to skin photocarcinogenesis and immunosuppression.

Commercial sunscreen products contain UV absorbers that chiefly protect against UV induced sunburn and DNA damage. Since, the biological endpoint for the determination of the SPF is the UV erythema. The SPF label is the indicator only for a protection against erythemally effective solar UV, largely confined to the UVB and partially short-wavelength UVA radiation. Hence, there is a continuous need of quantitative determination of different parameters, such as SPF, protection against UV radiations, to support the efficacy and safety of the products. For economical, practical and ethical reasons, there is an increasing curiosity employing in vitro methods because they are less time consuming, more cost-effective and give the additional information, for example critical wavelength and photostability. The in vitro method for SPF determination is preferred over in vivo methods because this can minimize risks related to UV exposure of human subjects during a sunscreen product development.

The in vitro screening method for SPF was examined by Kaur et al., *In vitro Sun Protection Factor Determination of Herbal Oils Used in Cosmetics*, Pharmacogn Res., 2010, 2, 1, 22-25 and Ashawat et al., *Photo protective properties of Boerhavia diffusa, Biosciences*, Biotech Res., 2006, 3, 257-60. Prepare 200 μg ml$^{-1}$ of the sample and determine absorbance values of the aliquot from 290 nm to 320 nm, at 5 nm intervals, using UV-Visible spectrophotometer. The observed absorbance values at 5 nm intervals (290-320 nm) were calculated by using the formula $$SPF_{Spectrophotometer} = CF \times \Sigma_{290}^{320} EE(\lambda) \times (\lambda) \times Abs(\lambda)$$

Where, CF is a correction Factor, EE ($\lambda$) is erythmogenic effect of radiation with wavelength $\lambda$ and Abs ($\lambda$) is spectrophotometric absorbance values at wavelength $\lambda$. The values of EE ($\lambda$)×I ($\lambda$) are constants.

The in vitro SPF studies of the prepared lotions, showed more SPF due to the presence of base, soybean antioxidants and nanoceria which accounts much to the stability and antioxidant effect to the lotions.

SPF Determination of Shifa Lotion:

| Wave length (nm) | EE ($\lambda$) × I ($\lambda$) employed | Absorbance (A) | EE ($\lambda$) × I ($\lambda$) × Absorbance (A) |
|---|---|---|---|
| 290 | 0.0150 | 3.6487 | 0.0547305 |
| 295 | 0.0817 | 3.5706 | 0.29171802 |
| 300 | 0.2874 | 3.4042 | 0.97836708 |
| 305 | 0.3278 | 3.1774 | 1.04155172 |
| 310 | 0.1864 | 3.1831 | 0.59332984 |
| 315 | 0.0837 | 2.7997 | 0.23433489 |
| 320 | 0.0180 | 2.766 | 0.049788 |

$\Sigma$ EE ($\lambda$) × I ($\lambda$) × A = 3.24382005
SPF = $\Sigma$ EE ($\lambda$) × I ($\lambda$) × A × 10 (Correction factor) = 3.244 × 10 = 32.44

SPF Determination of Shifa Nanoceria Lotion:

| Wave length (nm) | EE (λ) × I (λ) employed | Absorbance (A) | EE (λ) × I (λ) × Absorbance (A) |
|---|---|---|---|
| 290 | 0.0150 | 3.3904 | 0.050856 |
| 295 | 0.0817 | 3.4442 | 0.28139114 |
| 300 | 0.2874 | 3.3687 | 0.96816438 |
| 305 | 0.3278 | 3.3785 | 1.1074723 |
| 310 | 0.1864 | 3.3748 | 0.62906272 |
| 315 | 0.0837 | 2.8976 | 0.24252912 |
| 320 | 0.0180 | 2.9256 | 0.0526608 |

Σ EE (λ) × I (λ) × A = 3.33213646
SPF = Σ EE (λ) × I (λ) × A × 10 (Correction factor) = 3.332 × 10 = 33.32

SPF Determination of Aveeno Lotion:

| Wave length (nm) | EE (λ) × I (λ) employed | Absorbance (A) | EE (λ) × I (λ) × Absorbance (A) |
|---|---|---|---|
| 290 | 0.0150 | 3.3439 | 0.0501585 |
| 295 | 0.0817 | 3.1146 | 0.25446282 |
| 300 | 0.2874 | 2.8148 | 0.80897352 |
| 305 | 0.3278 | 2.6864 | 0.88060192 |
| 310 | 0.1864 | 2.601 | 0.4848264 |
| 315 | 0.0837 | 2.4142 | 0.20206854 |
| 320 | 0.0180 | 2.3043 | 0.0414774 |

Σ EE (λ) × I (λ) × A = 2.7225691
SPF = Σ EE (λ) × I (λ) × A × 10 (Correction factor) = 2.722 × 10 = 27.22

SPF Determination of Banana Boat Lotion:

| Wave length (nm) | EE (λ) × I (λ) employed | Absorbance (A) | EE (λ) × I (λ) × Absorbance (A) |
|---|---|---|---|
| 290 | 0.0150 | 3.0693 | 0.0460395 |
| 295 | 0.0817 | 3.0845 | 0.25200365 |
| 300 | 0.2874 | 2.9608 | 0.85093392 |
| 305 | 0.3278 | 2.9673 | 0.97268094 |
| 310 | 0 1864 | 2.9468 | 0.54928352 |
| 315 | 0.0837 | 2.6881 | 0.22499397 |
| 320 | 0.0180 | 2.5508 | 0.0459144 |

Σ EE (λ) × I (λ) × A = 2.9418499
SPF = Σ EE (λ) × I (λ) × A × 10 (Correction factor) = 2.941 × 10 = 29.418

SPF Determination of Herbal Lotion:

| Wave length (nm) | EE (λ) × I (λ) employed | Absorbance (A) | EE (λ) × I (λ) × Absorbance (A) |
|---|---|---|---|
| 290 | 0.0150 | 3.4302 | 0.051453 |
| 295 | 0.0817 | 3.2424 | 0.26490408 |
| 300 | 0.2874 | 3.0358 | 0.87248892 |
| 305 | 0.3278 | 2.8947 | 0.94888266 |
| 310 | 0.1864 | 2.8479 | 0.53084856 |
| 315 | 0.0837 | 2.7948 | 0.23392476 |
| 320 | 0.0180 | 2.7256 | 0.0490608 |

Σ EE (λ) × I (λ) × A = 2.95156278
SPF = Σ EE (λ) × I (λ) × A × 10 (Correction factor) = 2.951 × 10 = 29.51

SPF Determination of Herbal NC Lotion:

| Wave length (nm) | EE (λ) × I (λ) employed | Absorbance (A) | EE (λ) × I (λ) × Absorbance (A) |
|---|---|---|---|
| 290 | 0.0150 | 3.9292 | 0.058938 |
| 295 | 0.0817 | 3.8774 | 0.31678358 |
| 300 | 0.2874 | 3.9432 | 1.13327568 |
| 305 | 0.3278 | 3.9602 | 1.29815356 |
| 310 | 0.1864 | 3.8643 | 0.72030552 |
| 315 | 0.0837 | 3.9611 | 0.33154407 |
| 320 | 0.0180 | 3.9388 | 0.0708984 |

Σ EE (λ) × I (λ) × A = 3.92989881
SPF = Σ EE (λ) × I (λ) × A × 10 (Correction factor) = 3.93 × 10 = 39.3

SPF Determination of Nanoceria Lotion:

| Wave length (nm) | EE (λ) × I (λ) employed | Absorbance (A) | EE (λ) × I (λ) × Absorbance (A) |
|---|---|---|---|
| 290 | 0.0150 | 3.5214 | 0.052821 |
| 295 | 0.0817 | 3.2631 | 0.26659527 |
| 300 | 0.2874 | 2.9933 | 0.86027442 |
| 305 | 0.3278 | 2.8383 | 0.93039474 |
| 310 | 0 1864 | 2.7778 | 0.51778192 |
| 315 | 0.0837 | 2.6872 | 0.22491864 |
| 320 | 0.0180 | 2.5776 | 0.0463968 |

Σ EE (λ) × I (λ) × A = 2.89918279
SPF = Σ EE (λ) × I (λ) × A × 10 (Correction factor) = 2.899 × 10 = 28.99

The overall SPF values validate that formulated lotions with less number of ingredients and ease of synthesis are more effective in terms of protecting skin from UV rays. The comparative SPF values of the lotions are summarized in Table 4 below.

TABLE 4

| Lotion | SPF |
|---|---|
| Shifa | 32.44 |
| Shifa NC | 33.32 |
| Aveeno | 27.22 |
| Banana Boat | 29.4 |
| Herbal | 29.51 |
| Herbal NC | 39.3 |
| Nanoceria | 28.99 |

4. Determination of Elastase Inhibition

Elastin is an ECM protein and most abundant in organs providing elasticity to the connective tissues. It forms elastic fiber in the skin dermis and this may increase the skin elasticity. Damage to the elastin fibers leads to the declined skin resilience. The proteinase enzyme produced elastase, and this enzyme is able to erode elastin. Therefore, inhibition of the elastase activity ingredients could be used in cosmetic formulation to protect against skin aging and wrinkles.

Porcine pancreatic elastase was assayed spectrophotometrically using N-Succ-(Ala) 3-nitroanilide (SANA) as the substrate by Sahasrabudhe et al., *Anti-hyaluronidase, Anti-elastase Activity of Garcinia indica.*, Int. J. Botany, 2010, 1-5. The release of p-nitroaniline for 15 min at 25° C. is monitored by measuring the absorbance at 410 nm. The reaction mixture contained 800 μl of 0.2 M Tris buffer (pH 8.0), 100 μl of enzyme elastase and 100 μl of 0.8 mM SANA as substrate and test samples in Tris-HCl buffer. Pre-incubate the test sample with the enzyme for 20 min at 25° C. and the reaction is started with the addition of substrate. The buffer is used as control. The change in absorbance is monitored at 410 nm using UV spectrophotometer. Inhibitory effect of the samples on the Elastase activity calculated as:

$$\text{Percentage inhibition (\%)} = \frac{A - B}{A} \times 100$$

wherein A, is the absorbance at 410 nm without test sample, and B is the change in absorbance at 410 nm with the test sample.

Figure 34:
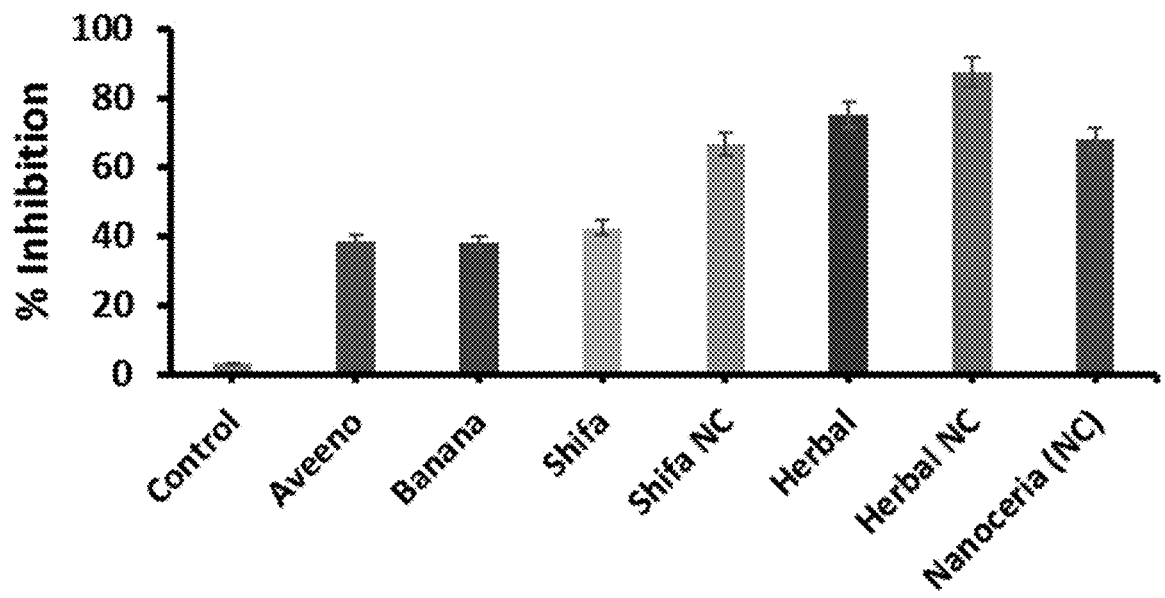
FIG. 34 is a graph comparing the % elastase inhibition of the identified lotions.

As shown in FIG. 34, Nanoceria and Herbal NC can inhibit elastase to maximum extent (90-80%). Whereas, other lotion and marketed lotions are close to each other, approximately 60-40%.

5. Determination of Collagenase Assay

The collagen is present in eighty percent of human skin and is responsible for the tensile strength of the skin. ROS leads to distinct changes in skin collagenous tissues by the breakdown of collagen, a major in the ECM. Collagen fibrils and elastin are responsible for strength and resiliency of skin. Aging and irradiation accelerate the degradation of the ECM, resulting in a decrease in dermal collagen and an increase in the level of the matrix MMP-1, which cleaves interstitial collagen leads the skin appear to be aged. Furthermore, collagenase activity has been required to inhibit for retention of skin elasticity and tensile strength of the skin.

The assay employed was based on spectrophotometric methods reported by Thring et al., *Anti-collagenase, Anti-elastase and Anti-oxidant activities of Extracts from 21 plants*, BMC Complement Altern. Med., 2009, 4, 9, 27, with some modifications for use in a microplate reader. The assay was performed in 50 mM Tricine buffer (pH 7.5 with 400 mM NaCl and 10 mM $CaCl_2$)). Dissolved collagenase from *Clostridium histolyticum* in the buffer for use at an initial concentration of 0.8 units/mL according to the supplier's activity data. The synthetic substrate N-[3-(2-furyl) acryloyl]-Leu-Gly-Pro-Ala (FALGPA) was dissolved in Tricine buffer to 2 mM. Incubate the sample with the enzyme in the buffer for 15 min before adding substrate to start the reaction. The final reaction mixture (150 μl total volumes) contained Tricine buffer, 0.8 mM FALGPA, 0.1 units *Clostridium histolyticum* and 25 μg test samples. Control is without test samples. Absorbance at 335 nm is measured immediately after adding substrate and then continuously for 20 min using a Cary 50 Microplate Reader in Nunc 96 well microtitre plates. Epigallocatechin-3-gallate, 250 μM (0.114 mg/ml) used as a positive control.

Figure 35:
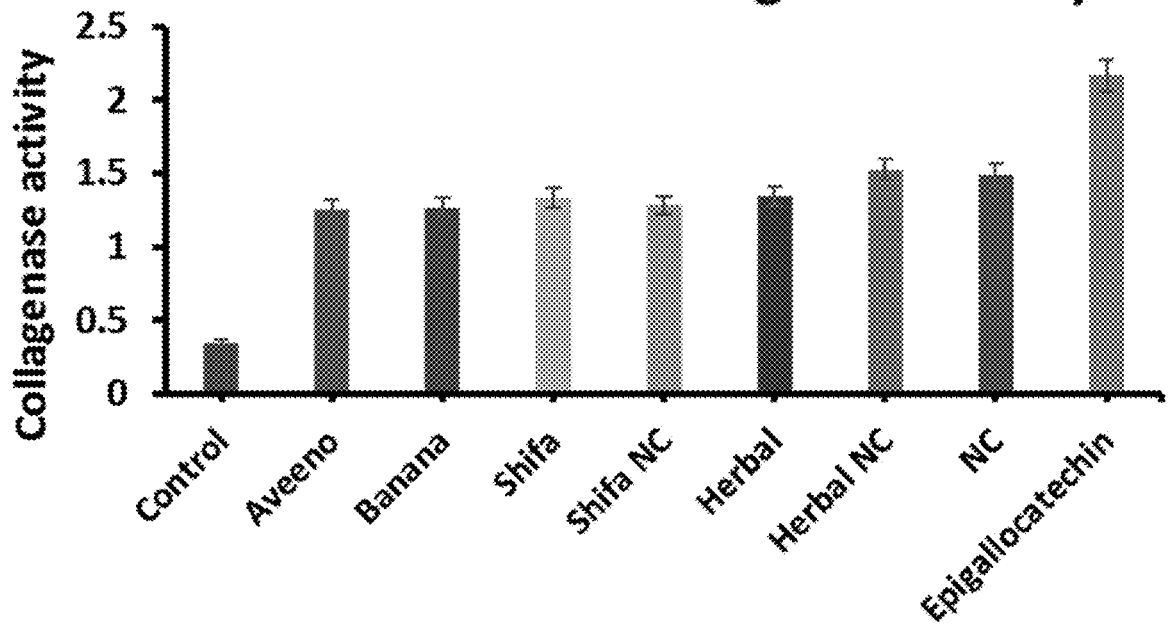
FIG. 35 is a graph comparing the Collagenase Assay results of the identified lotions, which tests how well a lotion protects the collagenase from being degraded by UV rays and ROS.

The results in FIG. 35 show how the lotions protect the collagenase from getting degraded by UV rays and ROS. All the lotions can inhibit degradation of collagen to almost same extent. Epigallocatechin was used as positive control.

6. DNA Repair Enzyme

Figure 36:
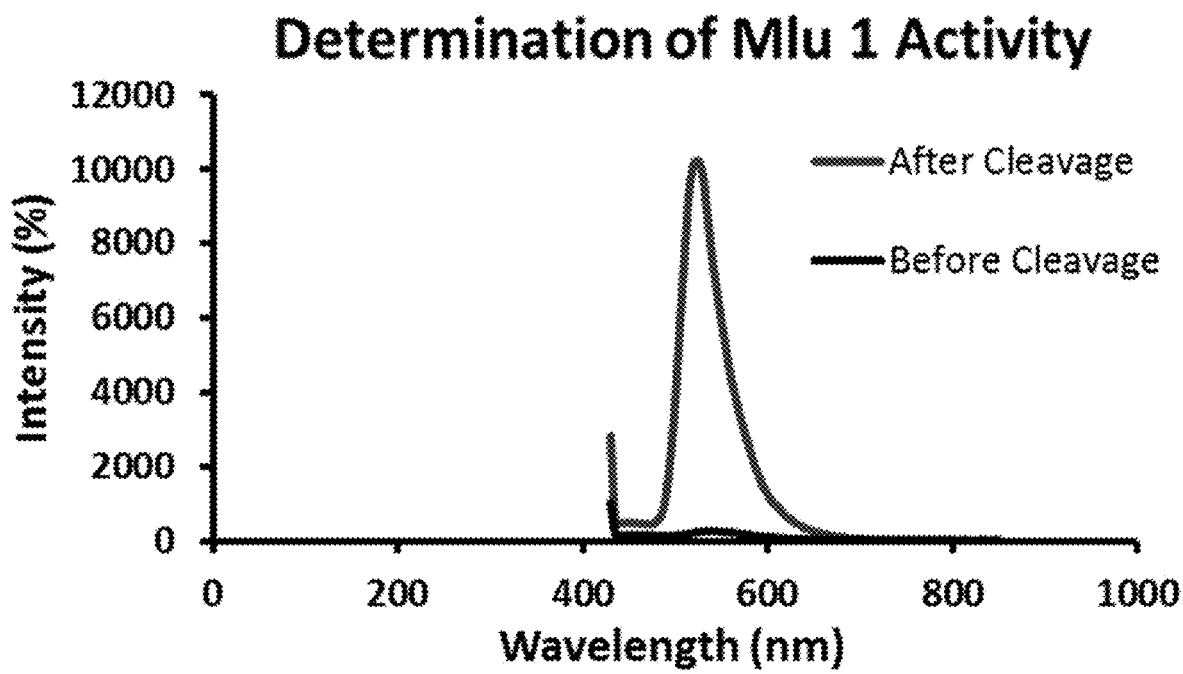
FIG. 36 is a graph of Mlu 1 enzyme activity.

DNA substrate with fluorophore and black hole quencher (substrate) is taken and is incubated with R buffer and Mlu 1 enzyme. Presence of black hole quencher quenches the fluorophore activity attached to DNA (FIG. 36, Before cleavage). When the substrate is incubated with enzyme at 37° C. for 1 h, the quencher attached to the substrate gets fissured and the fluorophore exerts its fluorescence activity. As a result, when assayed spectrophotometrically at an excitation wavelength of 490 nm and emission wavelength of 515 nm, the fluorophore gives the fluorescence peak confirming that the DNA is cleaved (After cleavage). According to the above principle, when the DNA is damaged due to UV rays and forms dimers, the enzyme incorporated in our lotion will cleave these dimers and allows normal replication of DNA thereby reducing the mutant gene expression and this can be observed by the fluorophore attached to it.

As shown in FIG. 36, DNA attached with fluorophore and quencher upon incubation with Mlu 1 enzyme gets cleaved and exhibits fluorescence. In the absence of enzyme, the quencher quenches the fluorescence activity of fluorophore.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A polyethylene glycol-functionalized triglyceride polyol polymer comprising a glycerol component and three fatty acid components bonded to the glycerol component, wherein each fatty acid component comprises a fatty acid chain and at least one of the fatty acid components further comprises:

a hydroxyl functional group bound to a carbon atom of the fatty acid chain; and a polyethylene glycol-based functional group bound to an adjacent carbon atom of the fatty acid chain;

according to Structure I below

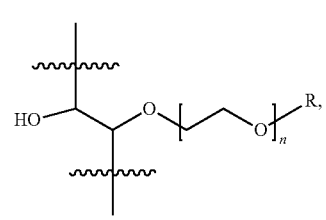

(I)

wherein:

n is from 10 to 40; and

R is selected from the group consisting of H, alkyl, and silyl; and wherein the fatty acid chains of the three fatty acid components are not crosslinked via ether linkages.

2. The polymer of claim 1, wherein three of the fatty acid components comprise Structure I.

3. The polymer of claim 1, wherein at least one of the fatty acid components comprises more than one Structure I.

4. The polymer of claim 1, wherein R is $CH_3$.

5. The polymer of claim 1, wherein the fatty acid chain(s) independently comprises between 12 and about 20 carbon atoms.

6. The polymer of claim 1, wherein the triglyceride of the polyethylene glycol-functionalized triglyceride polyol polymer is a constituent of a vegetable oil selected from the group consisting of soybean oil, corn oil, palm oil, sunflower oil, canola oil, sesame oil, peanut oil, olive oil, cottonseed oil, avocado oil, almond oil, walnut oil, flaxseed oil, and combinations thereof.

7. The polymer of claim 1, which is free of polyethylene glycol groups between the glycerol component and the fatty acid components of the triglyceride.

8. A topical lotion comprising a base component, wherein the base component comprises a polyethylene glycol-functionalized triglyceride polyol polymer comprising a glycerol component and three fatty acid components bonded to the glycerol component, wherein each fatty acid component comprises a fatty acid chain and at least one of the fatty acid components further comprises:
  a hydroxyl functional group bound to a carbon atom of the fatty acid chain; and
  a polyethylene glycol-based functional group bound to an adjacent carbon atom of the fatty acid chain;
according to Structure I below

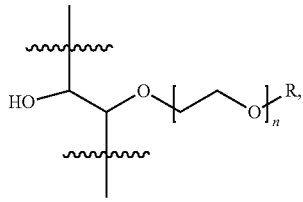

(I)

wherein:
  n is from 10 to 40; and
  R is selected from the group consisting of H, alkyl, and silyl; and
wherein the fatty acid chains of the three fatty acid components are not crosslinked via ether linkages.

9. The topical lotion of claim 8, wherein the polyethylene glycol-functionalized triglyceride polyol polymer is at an amount in a range of about 40% to about 80% by weight of the topical lotion.

10. The topical lotion of claim 8 further comprising one or more of the following:
  an antioxidant isoflavone component selected from the group consisting of daidzein, genistein, and combinations thereof at an amount in a range of about 2% to about 6% by weight of the topical lotion;
  an antioxidant nanoparticle component that comprises a metal oxide that is selected from the group consisting of cerium oxide, manganese oxide, iron oxide, and combinations thereof at an amount in a range of about 2% to about 6% by weight of the topical lotion;
  a DNA repair enzyme component that is a nucleic acid at an amount in a range of about 1% to about 4% by weight of the topical lotion; and
  an herbal extract component selected from the group consisting of alkaloids, flavonoids, and combinations thereof at an amount in a range of about 1% to about 4% by weight of the topical lotion.

11. A method of preparing a polyethylene glycol-functionalized triglyceride polyol polymer, the method comprising:
  reacting an expoxidized triglyceride that comprises a glycerol component and three fatty acid components bonded to the glycerol component, wherein each fatty acid component comprises a fatty acid chain and at least one of the fatty acid components further comprises at least one epoxide functional group bound to two adjacent carbon atoms of the fatty acid chain;
  with a polyethylene glycol-based polymer in the presence of an acidic catalyst that is a non-aqueous tetrafluoroboric acid ether complex to open the epoxide functional group and form:
    a hydroxyl functional group bound to one of said adjacent carbon atoms of the fatty acid chain; and
    a polyethylene glycol-based functional group bound to the other of said adjacent carbon atoms of the fatty acid chain;
  according to Scheme I

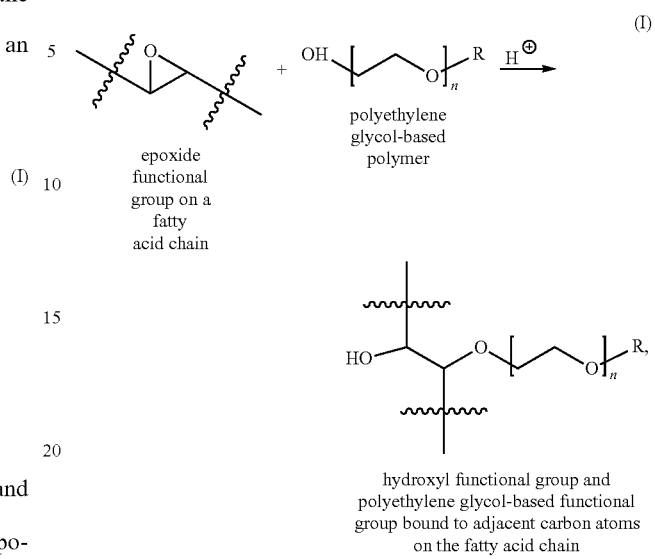

(I)

wherein:
  n is from 10 to 40; and
  R is selected from the group consisting of H, alkyl, and silyl; and
  wherein the fatty acid chains of the three fatty acid components are not crosslinked via ether linkages;
thereby producing the polyethylene glycol-functionalized triglyceride polyol polymer.

12. The method of claim 11, wherein three of the fatty acid components comprise the hydroxyl functional group bound to one of said adjacent carbon atoms of the fatty acid chain and the polyethylene glycol-based functional group bound to the other of said adjacent carbon atoms of the fatty acid chain.

13. The method of claim 11, wherein at least one of the fatty acid components comprises more than one of the hydroxyl functional groups and more than one of the polyethylene glycol-based functional groups.

14. The method of claim 11, wherein R is $CH_3$.

15. The method of claim 11, wherein the fatty acid chain(s) independently comprises between 10 and about 20 carbon atoms.

16. The method of claim 11, wherein the triglyceride of the epoxidized triglyceride is a constituent of a vegetable oil constituent selected from the group consisting of soybean oil, corn oil, palm oil, sunflower oil, canola oil, sesame oil, peanut oil, olive oil, cottonseed oil, avocado oil, almond oil, walnut oil, flaxseed oil, and combinations thereof.

17. The method of claim 11, which is free of polyethylene glycol groups between the glycerol component and the fatty acid components of the triglyceride.

18. The method of claim 11, wherein the reaction is conducted in the absence of a solvent.

19. The method of claim 11, wherein the reaction is conducted in the presence of a solvent.

20. The method of claim 11, wherein the reaction is conducted at a temperature in a range about 50° C. and about 60° C.

* * * * *